US008541400B2

(12) United States Patent
Johnsson et al.

(10) Patent No.: US 8,541,400 B2
(45) Date of Patent: Sep. 24, 2013

(54) COMPOSITIONS FORMING NON-LAMELLAR DISPERSIONS

(75) Inventors: Markus Johnsson, Lund (SE); Fredrik Joabsson, Lund (SE); Fredrik Tiberg, Lund (SE)

(73) Assignee: Camurus AB, Lund (SE)

( * ) Notice: Subject to any disclaimer, the term of this patent is extended or adjusted under 35 U.S.C. 154(b) by 1381 days.

(21) Appl. No.: 11/658,857

(22) PCT Filed: Aug. 4, 2005

(86) PCT No.: PCT/GB2005/003056
§ 371 (c)(1),
(2), (4) Date: Jul. 20, 2007

(87) PCT Pub. No.: WO2006/013369
PCT Pub. Date: Feb. 9, 2006

(65) Prior Publication Data
US 2008/0161276 A1    Jul. 3, 2008

(30) Foreign Application Priority Data

Aug. 4, 2004 (GB) ................................. 0417388.6
Nov. 23, 2004 (GB) ................................. 0425754.9

(51) Int. Cl.
*A61K 47/14* (2006.01)
*A61K 31/57* (2006.01)
*A61K 31/216* (2006.01)
*A61K 31/565* (2006.01)
*A61K 31/496* (2006.01)
*A61K 31/05* (2006.01)
*A61K 31/404* (2006.01)

(52) U.S. Cl.
USPC ...... 514/178; 514/543; 514/414; 514/254.07; 514/407; 514/731; 514/786; 514/182

(58) Field of Classification Search
None
See application file for complete search history.

(56) References Cited

U.S. PATENT DOCUMENTS

| | | | | |
|---|---|---|---|---|
| 5,531,925 A | * | 7/1996 | Landh et al. | 252/299.01 |
| 6,403,122 B1 | | 6/2002 | Andrysek et al. | |
| 2003/0022242 A1 | | 1/2003 | Anderson | |
| 2003/0108743 A1 | | 6/2003 | Anderson | |

FOREIGN PATENT DOCUMENTS

WO    WO 9306921    *    4/1993

OTHER PUBLICATIONS

Pitzalis et al (Langmuir, 2000, 16, p. 6358).*
Borne, Langmuir, 2000, 16, p. 10044.*
Srisiri Langmuir, 1998, 14, p. 1921.*
International Search Report for PCT/GB2005/003056 mailed May 2, 2006.

* cited by examiner

*Primary Examiner* — David J Blanchard
*Assistant Examiner* — Thurman Wheeler
(74) *Attorney, Agent, or Firm* — Nixon & Vanderhye P.C.

(57) ABSTRACT

The present invention relates to compositions containing a) at least one monoacyl lipid; b) at least one diacyl glycerol and/or tochopherol; and c) at least one fragmentation agent; and optionally an active agent. The compositions are capable of self-dispersing to provide colloidal non-lamellar particles upon contact with an aqueous fluid. The invention additionally provides a method for forming non-lamellar particles from such compositions, and pharmaceutical formulations containing the compositions, plus non-lamellar particles formable from the compositions.

22 Claims, 11 Drawing Sheets

COMPOSITIONS FORMING NON-LAMELLAR DISPERSIONS

This application is the U.S. national phase of international application PCT/GB2005/003056 filed 4 Aug. 2005, which designated the U.S. and claimed priority of GB 0417388.6 filed 4 Aug. 2004 and GB 0425754.9 filed 23 Nov. 2004, the entire contents of each of which are hereby incorporated by reference.

The present invention relates to an amphiphile composition suitable for use in preparing formulations for administration to human or animal subjects. In particular the present invention relates to such compositions which are capable of self-dispersion to provide dispersions of micrometer and sub-micrometer sized non-lamellar particles.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature, these phases may be described as normal (mean curvature towards the apolar region) or reversed (mean curvature towards the polar region). Where the spontaneous curvature of the lipid system is low, the structures are typically lamellar, such as mono- or multi-lamellar vesicles and liposomes and where the spontaneous curvature is higher, liquid crystalline phases or micellar phases dominate.

The non-lamellar liquid crystalline and L3 phases are thermodynamically stable systems. That is to say, they are not simply a meta-stable state that will separate and/or reform into layers, lamellar phases or the like, but are the stable thermodynamic form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area and tuneable interior space-dividing mesophase structure comprising both polar and apolar nanodomains. This has led to considerable investigation of non-lamellar phases particularly in controlled-release formulations and for solubilising relatively insoluble compounds.

In order to assess the presence of a liquid crystalline phase, the liquid crystalline order discussed above may be examined by use of small-angle X-ray diffraction (SAX), cryo-Transmission Electron Microscopy (cryo-TEM) or Nuclear Magnetic Resonance (NMR) spectroscopy studies. Cryo-TEM may also be used to examine and identify other amphiphile phase structures. The sizes and size distributions of the dispersed particles may be examined by light scattering, particularly by use of laser light scattering instruments.

As discussed above, a bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk non-miscible phase would cause problems, such as in parenteral applications. Further control of a compound's release profile may also be achieved by such a dispersion.

The dispersion of non-lamellar phase into particles is essential for this amphiphile phase structure to be of value in certain (particularly in vivo) applications.

In general, the dispersion of non-lamellar phases requires a relatively high energy input and generally requires specialised apparatus. Typical methods include ultrasonication, homogenisation and high pressure filtration. Examples of such "high energy produced" non-lamellar particles can be found in the literature (Kamo et al., Langmuir, 2003, 19, 9191-95 and Gustafsson et al., Langmuir, 1997, 13, 6964-71).

These high energy dispersion methods have a number of disadvantages. For example, dispersions cannot typically be generated at the point of care because of the time equipment and specialised manufacturing methods required. Such dispersions must therefore be transported, handled and stored while containing up to 99% by weight of water. This obviously makes transport and storage difficult and also means that the dispersion particle properties such as loading level and particle size must be stable to transport and storage over a considerable period. Furthermore, the manufacturing time and costs are considerable.

The use of high energy dispersion techniques also restricts the range of active agents which can be incorporated into non-lamellar amphiphile particle dispersions. In particular, shear and/or heat sensitive active agents such as proteins and/or peptides are insufficiently robust to allow the use of high energy dispersion methods. The alternative being to add the active agent after the dispersion is formed, which is not only time consuming but can produce insufficient or unpredictable loading levels.

A high energy method for the formation of dispersed particles of non-lamellar phase in solvents such as water is described in U.S. Pat. No. 5,531,925. Such particles have a non-lamellar liquid crystalline or L3 interior phase and a lamellar or L3 surface phase and may also contain active ingredients.

It is evident that there exists a considerable need for compositions and methods allowing dispersions of non-lamellar phase particles to be generated without employing high energy dispersion methods. It would be a significant advantage if the particles formed were colloidal and it would also be a considerable advantage if the resulting particles were well tolerated in vivo.

The present inventors have now established that compositions comprising monoacyl lipids, diacyl glycerols and/or tocopherols, fragmentation agents and optionally active agents have the surprising property that they form self-dispersing compositions which generate colloidal non-lamellar phase particles upon exposure to aqueous conditions without requiring the use of high energy techniques.

In a first aspect, the present invention thus provides a composition comprising
a) at least one monoacyl lipid;
b) at least one diacyl glycerol, at least one tocopherol, or mixtures thereof and
c) at least one fragmentation agent;
and optionally an active agent, wherein the composition is capable of self-dispersing to provide (preferably colloidal) non-lamellar particles upon contact with an aqueous fluid.

In a preferred aspect, the invention provides a composition comprising
a) at least one monoacyl lipid;
b) at least one diacyl glycerol; and
c) at least one fragmentation agent;
and optionally an active agent, wherein the composition is capable of self-dispersing to provide (preferably colloidal) non-lamellar particles upon contact with an aqueous fluid.

It is a notable advantage of the present invention that dispersions of non-lamellar particles can be formed without the need for high energy fragmentation methods or specialised equipment. This allows formation of the dispersion at the time, and place required, such as at the point of care.

In another aspect, the present invention thus provides a method for the formation of a dispersion of non-lamellar particles, said method comprising contacting a composition comprising
a) at least one monoacyl lipid;
b) at least one diacyl glycerol, at least one tocopherol, or mixtures thereof and
c) at least one fragmentation agent;
with an aqueous fluid and optionally subjecting the thus-formed mixture to a low energy agitation method. Examples of suitable methods include manual stirring and/or manual shaking and mechanical shaking at up to 350 rpm.

In a preferred aspect, component b) is at least one diacyl glycerol.

The non-lamellar particles formed by self-dispersion of the compositions of the present invention are also of a unique composition and thus form a further aspect of the invention.

In a further aspect, the present invention thus provides colloidal non-lamellar particles comprising
a) at least one monoacyl lipid;
b) at least one diacyl glycerol, at least one tocopherol, or mixtures thereof and
c) at least one fragmentation agent;
optionally and active agent and optionally an aqueous fluid.

In a preferred aspect, component b) is at least one diacyl glycerol.

The compositions of the present invention are highly suitable for allowing the preparation of colloidal dispersions outside of a dedicated manufacturing facility, such as at the point of care. This offers advantages in case the active agent may not be stable in solution or dispersion for long periods or if there is any concern over the particle-size stability of the dispersion to storage. Such "prepared on demand" type dispersions are most easily supplied in the form of a kit containing the essential elements required for dispersion preparation.

In a still further aspect, the present invention thus provides a kit for the preparation of a dispersion of non-lamellar particles, said kit comprising a composition comprising;
a) at least one monoacyl lipid;
b) at least one diacyl glycerol, at least one tocopherol, or mixtures thereof and
c) at least one fragmentation agent;
and optionally an active agent.

In a preferred aspect, component b) is at least one diacyl glycerol.

Suitable kits may also, optionally, include items such as at least one vessel suitable for carrying out the preparation of the dispersion (e.g. a re-sealable tube of suitable capacity which can be manually shaken), at least one aqueous fluid (preferably pre-measured) suitable for use in preparing the dispersion (e.g. isotonic saline for injection) and/or instructions regarding preparation of the dispersion. The active agent, where present, may be formulated with the amphiphile components or may be present as a separate compartment for inclusion when the dispersion is prepared.

The compositions of the invention will desirably be formulated with an active agent, as indicated herein below. Where such an active agent is a drug, diagnostic agent, vaccine, prophylactic agent or similar pharmaceutical active then, in a further aspect, the present invention provides a pharmaceutical formulation comprising a composition of the invention, at least one active agent and optionally at least one pharmaceutically acceptable carrier or excipient.

By the term "self dispersing" as used herein is indicated a composition which does not require the presence of organic solvents (hydrotropes) or high energy techniques such as homogenization, ultrasonication or vigorous mechanical shaking in order to create a colloidal dispersion. A composition can be considered "self dispersing" if the solvent-free composition is capable of forming a dispersion of non-lamellar particles with a monomodal size distribution with an average size no larger than 5 μm and a distribution width of no larger than 3 μm at half height by a method comprising forming a 5 wt % solution in an aqueous fluid (such as water or aqueous buffer) and shaking for up to 12 hours at up to 350 rpm.

Although compositions of the present invention may contain solvents/hydrotropes, the presence of these agents is not necessary for the self-dispersion. Thus, the compositions are all capable of self dispersion in the absence of any solvent or hydrotrope even if such agents are included in the compositions for other reasons (such as to provide a convenient liquid composition).

The term "self-dispersing" indicates self-dispersion from a bulk solid or liquid lipid mixture or solution (e.g. with up to 15%, preferably up to 10% by weight added solvent) but does not encompass self-dispersion where a lipid mixture has previously been fragmented by use of hydrotropes or a high energy technique and subsequently dried in finely divided powder form such that each particle is ready formed for rehydration. The compositions of the invention are "self-dispersing" in that they inherently possess the properties required to generate a colloidal dispersion, as indicated above. Thus, bulk compositions which consist of, for example, coated micron sized particles are not "capable of self-dispersion" unless the particles could be created by self-dispersion, as described herein, followed by drying. Previously known compositions use hydrotropes and/or high energy techniques followed by drying and such compositions are thus not capable of self-dispersion.

It has been known in the art to provide self-dispersing compositions which generate largely lamellar and/or micellar phase particles and it has also been known, as discussed above to provide bulk non-lamellar phases which may be dispersed by the input of significant energy, such as in the form of shearing force, high pressure extrusion or ultrasound. It has also been shown that dispersed non-lamellar particles may be obtained by including a co-solvent/hydrotrope such as ethanol into the lipid mixture and thereafter diluting the mixture into aqueous solution (Spicer et al., Langmuir, 2001, 17, 5748-56). Self-dispersion in the present context, however does not require the presence of any solvent or the use of any high energy method.

Typical previously known non-lamellar compositions are not treated with homogenization, ultra sonication or hydrotropes simply to speed up the process of dispersion but because they are inherently incapable of self-dispersion. Even though previously known techniques for producing non-lamellar dispersions employ high energies or hydrotropes, they continue to produce a significant amount of lamellar (vesicular) particles (see, for example Spicer supra) and typically also result in broad and/or ill-defined size distributions (such as bi- or multi-modal distributions and/or quantities of macroscopic particles e.g. particles larger than 100 μm). Furthermore, the storage stability of previously known high-energy or hydrotrope produced non-lamellar dispersions is generally low. In such previous dispersions the mean particle size and/or width of size distribution and/or the particle phase behaviour is not stable to storage. This is especially so in the case of dispersed non-lamellar reversed hexagonal particles (Kamo et al., Langmuir, 2003, 19, 9191-95).

As illustrated in the comparative Example 11 herein, previously known compositions do not form non-lamellar well-defined particle dispersions of colloidal-type size in the absence of high energy techniques and/or hydrotropes. The present compositions, however, allow the advantages of non-lamellar phase particles (in particular non-lamellar reversed hexagonal phase particles) to be accessed without the need for high energies, specialised equipment and/or co-solvents/hydrotropes. The compositions furthermore generate reproducible and reliable particle size distributions within the colloidal size range, which are highly stable to storage.

As used herein, the term "non-lamellar" is used to indicate a normal or reversed liquid crystal phase (such as a cubic or hexagonal phase) or the L3 phase or any combination thereof, as opposed to lamellar structures such as vesicles/liposomes. Where a particle is described as having a non-lamellar phase or form, this indicates that at least the internal region of the particle should adopt this form. The particles will generally have two distinct regions, an internal region and a surrounding surface region. The surface region, even in a "non-lamellar" particle will often be lamellar or crystalline and may be any phase ranging from a highly ordered crystalline or liquid crystal phase to a virtually orderless fluid layer. In contrast, a "lamellar" particle, as described herein is a particle having a solvent, rather than non-lamellar, core-region. In an alternative but less preferred aspect, non-lamellar as used herein may also refer to normal and/or reversed micellar phase structures.

It is preferred that compositions of the present invention form reversed non-lamellar phase particles and more preferred that the compositions form reversed liquid crystalline phase particles such as bicontinuous cubic or reversed hexagonal liquid crystalline phase. Since the non-lamellar phase structure forms by self-dispersion in aqueous fluid, it is evident that this phase structure should be in or near equilibrium with the bulk solvent phase. This is typically represented by the presence of a multi-phase region in the phase diagram with a non-lamellar phase co-existing with a bulk solvent phase. This is also clearly reflected in the stability of the dispersions as discussed herein below.

It is a highly advantageous feature of the present invention that the compositions may be chosen to provide stable reversed hexagonal liquid crystalline particles in colloidal dispersion. Reversed hexagonal colloidal particles are less commonly generated with known amphiphile mixtures and few stable dispersions of such particles have been demonstrated. The Examples below demonstrate that the present invention provides not only dispersions of hexagonal liquid crystalline particles but such dispersions which have narrow, colloidal, particles size distributions and are stable to prolonged storage.

In some circumstances, compositions of the present invention will self-disperse to form partially non-lamellar particles and partially lamellar and/or micellar particles but more than 50% of the amphiphile should disperse to be comprised in non-lamellar structures. It is preferred that at least 70% of the amphiphile is formed by self-dispersion of the compositions of the present invention into non-lamellar particles, more preferred that at least 75% and most preferred that at least 85% of the amphiphile self-disperses to be comprised in non-lamellar particles.

As indicated above, the compositions of the present invention will be self-dispersing to provide particles with a monomodal size distribution and an average particle size of no more than 5 μm. It is preferable that this average particle size be no more than 2 μm and more preferable that this be no more than 1 μm. The width of the particle size distribution should also be narrow, preferably being no more than 3 μm at half-height, more preferably no more than 1 μm and most preferably no wider than 0.5 μm at half-height. Such particles can be considered colloidal and are suitable for administration (as a dispersion in a suitable fluid) directly to a subject, such as by intravenous injection. If there is any significant proportion of particles above around 8 μm then administration of such dispersions to the blood stream of a subject can cause dangerous reactions such as embolism. It is believed to be a unique and highly advantageous property of the compositions of the present invention that they can spontaneously disperse to provide particles in the colloidal, micron or sub-micron particle size range with no detectable particles above 8 μm and in some cases no detectable particles with sizes above 1 μm. A narrow and predictable size distribution is advantageous in all administration routes (e.g. oral, nasal, buccal etc.) to provide control over active agent transport and release.

The components for use in the compositions of the present invention include a) at least one monoacyl lipid, b) at least one diacyl glycerol, at least one tocopherol, or mixtures thereof and c) at least one fragmentation agent. In a preferred aspect, component b) comprises or consists of at least on diacyl glycerol.

As component a) of the compositions of the present invention is employed a monoacyl lipid. Preferred species of such lipids include monoacyl oligoglycerols such as mono- or preferably di-, tri- or tetra-glycerols and pegylated glyceryl fatty acid esters, as well as pegylated fatty acids. In all of these cases, the acyl/fatty acid chains will typically have 12 to 22 carbons and 0, 1, 2 or 3 unsaturations. Preferred acyl/fatty acid groups include, for example, lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) groups, where CX:Y indicates a hydrocarbon chain having X carbon atoms and Y unsaturations Particularly preferred specific monoacyl lipids include Diglycerolmonooleate (DGMO), Diglycerolmonolinoleate (DGML) and Polyethyleneglycol(5)-glyceryl-monooleate (TMGO-5).

The component a) typically forms a micellar or preferably lamellar phase on contact with water. This can be tested by adding water to the material, equilibrating the sample and then determining the phase(s) present in the sample by small angle x-ray scattering (SAXS). It is preferred that the monoacyl component forms a lamellar phase upon contact with water. As an example, DGMO forms a lamellar phase that takes up a maximum of about 40 wt % water.

As component b) of the compositions of the invention is employed a diacyl glycerol, a tocopherol or mixtures thereof. The diacyl glycerol component are preferred as part or all of component b) and may be symmetrical or non-symmetrical diacyl lipids and each fatty acid group may be saturated or unsaturated. Preferred diacyl glycerols include those with acyl groups each having 12 to 22 carbons and 0, 1, 2 or 3 unsaturations. Preferred acyl groups include, for example, lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) where CX:Y indicates a hydrocarbon chain having X carbon atoms and Y unsaturations. A particularly preferred diacyl glycerol is glycerol dioleate (GDO).

As used herein, the term "a tocopherol" is used to indicate the non-ionic lipid tocopherol, often known as vitamin E, and/or any suitable salts and/or analogues thereof. The most preferred of the tocopherols is tocopherol itself, having the structure below. Evidently, particularly where this is purified from a natural source, there may be a small proportion of non-tocopherol "contaminant" but this will not be sufficient to alter the advantageous self dispersion properties and/or phase-behaviour of the composition. Typically, a tocopherol will contain no more than 10% of non-tocopherol-analogue compounds, preferably no more than 5% and most preferably no more than 2% by weight.

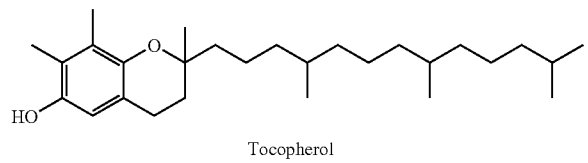 [SMILES: Cc1c(O)cc2c(c1C)OC(C)(CCCC(C)CCCC(C)CCCC(C)C)CC2]

Tocopherol

The b) component typically forms reversed liquid crystalline phases, such as reversed cubic or hexagonal phases, or a liquid L2 phase on contact with water. The b) component may also be an (especially surface active) oil taking up virtually no water. Again this can be tested by SAXS (see above) or determined by visual inspection by someone skilled in the art. It is preferred that the diacyl glycerol and/or the tocopherol forms an oil or L2 phase upon contact with water. As an example, GDO takes up very little water and separates out as an oily material when contacted with water.

As component c) can function any amphiphile capable of serving as a fragmentation agent with the selected components a) and b). A fragmentation agent is a (pure or mixed) agent which allows the composition comprising components a) and b) to self-disperse to form non-lamellar particles, as indicated herein.

There are a number of different molecular classes that are suitable as fragmentation agents in the present invention. These include;
1) Polymeric agents: Poloxamers (preferably Pluronic® F127, Pluronic® F68, Pluronic® F108 Pluronic® L44), 2-Methacryloyloxyethyl phosphorylcholine n-butyl methacrylate co-block polymers (such as PUREBRIGHT MB-37-50T and PUREBRIGHT MB-37-100T from NOF Corp.), pegylated sorbitan fatty acid esters (polysorbates, particularly Polysorbate 80), PEGylated surfactants (e.g. Solutol HS15 from BASF), pegylated castor oil derivatives (e.g. Cremophor EL, Cremophor RH40), pegylated fatty acids (e.g. PEG-oleate), pegylated phospholipids (including DOPE-PEG(2000), DOPE-PEG(5000) and DSPE-PEG(5000)), polyglycerin(PG)-phospholipids (such as DSPE-PG, for example, SUNBRIGHT DSPE-PG8G from NOF Corp., DOPE-PG), pegylated oligoalkylsorbitols (such as PEG-60 Sorbitoltetraoleate, e.g. GO-460V from Nikko Chemicals), pegylated glyceryl fatty acid esters (e.g. TMGO-15 (Nikko Chemicals)), pegylated tocopherols such as d-alpha tocopheryl polyethylene glycol 1000 succinate (Vitamin E TPGS (Eastman)) and pegylated alkyl ethers;
2) Polyol surfactants: sugar derived alkyl esters (such as sucrose laurate and sucrose oleate), sugar derived alkyl ethers (e.g. octyl glucoside);
3) Proteins: including casein, sodium caseinate, lysozyme;
4) Anionic surfactants: Carboxylates of fatty acids (especially sodium oleate, sodium palmitate, sodium stearate, sodium myristate), alkyl sulfates (such as sodium dodecyl sulphate (SDS)); and
5) Cationic surfactants: alkyl ammonium salts (including dodecyl trimethyl ammonium bromide (DTAB), cetyl trimethyl ammonium bromide (CTAB) and oleyl ammonium chloride).

The majority of the c)-components form normal micellar (L1) phases on contact with excess water. However, the components need not form micelles to function as fragmentation agents. The effective functioning of a fragmentation agent will easily be tested by a skilled worker by preparing appropriate compositions and conducting simple tests as illustrated in the Examples herein.

In one alternative embodiment of the present invention, component c) may be a monoacyl (especially non-naturally occurring) lipid. This will most commonly be where component c) is a polymeric mono-acyl lipid falling within category 1) above. In this embodiment, component c) may be fully or partially made up from one of more of the mono-acyl lipid constituents of component a). The only essential feature of this embodiment is that there should be sufficient fragmentation effect to provide for effective self-dispersion and/or stabilisation as described herein. Where this fragmentation effect can be provided by one or more mono-acyl lipid constituents of component a), which will typically occur where component a) comprises at least one non-naturally occurring monoacyl lipid, then this component will also serve as fragmentation agent c). Where some but insufficient fragmentation effect is provided by component a) then the content of additional fragmentation agent contributing to component c) will be correspondingly decreased.

In general, the components a), b) and c) will be present in the following proportions (where a, b and c are the weights of components a), b) and c) respectively); a/(a+b) is between 0.2 (e.g. 0.3) and 0.9 (e.g. 0.8) and c/(a+b+c) is between 0.01 and 0.3 (or corresponding appropriately to all or part of component a) where component a) includes a fragmentation agent). Compositions within this range have a high tendency to self-disperse under relatively mild conditions, without requiring high energy input. It is preferred, in order to provide easiest self-dispersion and greatest particle size control that the proportions of a), b) and c) are such that a/(a+b) is between 0.25 (e.g. 0.35) and 0.80 (e.g. 0.75), more preferably 0.35 (e.g. 0.4) and 0.75 (e.g. 0.65) and c/(a+b+c) is between 0.03 and 0.25 (e.g. 0.2) (where a, b and c are the weights of components a), b) and c) respectively).

The compositions of the present invention may also comprise an active agent and/or other amphiphilic components. For example, charged (especially anionic) lipids/fatty acids may be included so that higher loading levels of active agent may be obtained (such as for a cationic peptide e.g. octreotide). Example types of additional components are charged lipids or surfactants (e.g. Dioleoyl phosphatidylglycerol (DOPG), oleic acid (OA), Dioleoyltrimethyl ammonium propane (DOTAP)) and polymeric surface modifiers.

Preferred polymeric surface modifiers include polyethylene oxide copolymers and lipids derivatised with polyethylene oxide, polysaccharides (such a chitosan), hydrophobically modified polysaccharides and amphiphilic proteins. Poloxamers are particularly suitable as the polymeric components as are PEG-substituted lipids such as PEG-glyceroldioleate, PEG-dioleoyl phosphatidyl ethanolamine (in particular DOPE-PEG2000 and DOPE PEG-5000) or PEG-dioleoyl phosphatidyl serine. Suitable polymeric agents also include PEG-sorbitol tetraolete (Nikko), cholesterol pullulan (NOF) and 2-Methacryloyloxyethyl phosphorylcholine n-butyl methacrylate co-block polymers (PUREBRIGHT MB-37-50T and PUREBRIGHT MB-37-100T from NOF).

The compositions of the invention may be solid, for example powder, compositions or may be liquid precursor compositions, of pure amphiphile and active agent (plus optional excipients) without the need for any solvent or hydrotrope. In one preferred embodiment, the present compositions are provided as solvent free formulations either for dispersion prior to administration or for direct administration in solvent-free form. This has advantages in convenience and ease of administration as well as avoiding unnecessary administration of organic solvent In an alternative embodiment, liquid compositions of the invention may be prepared as solvent mixtures. Such liquid precursors will comprise components a, b, c, a cosolvent and optionally an active agent. The liquid precursors containing an active agent can, for example, be filled in capsules and because of the self-dispersing ability of the composition, non-lamellar particles form when contacted with GI-fluid. Similarly, a liquid precursor may be provided in an ampoule for dispersion in a fluid (e.g. isotonic saline) prior to injection.

Co-solvents should generally be miscible, to at least some extent with water and should be tolerable in the application in which the composition will be used (e.g. biotolerable). Organic solvents having 1 to 6 carbon atoms and preferably at least one oxygen substituent and water-soluble polymers thereof are preferred. Suitable classes of cosolvents are alcohols (including polyols), ketones, esters, ethers, and polymers thereof. Typical co-solvents are ethanol, N-methyl-2-pyrrolidone (NMP), propylene glycol, dimethylacetamide (DMA), glukofurol, transcutol, PEG400 and glycerol added up to about 15%, preferably up to about 10% (by weight) of total lipid.

In a further alternative embodiment, the invention provides solid or semi-solid (e.g. gel, waxy solid) compositions which may be prepared by use of a polymeric agent in the compositions of the invention. Such solid or semi-solid precursors will comprise compositions of the invention as described herein and additionally at least one polymeric solidifying agent. Typically, such compositions comprise components a, b, c, a polymeric agent, optionally a cosolvent and optionally an active agent. The solid or semi-solid precursors are typically liquefiable by heat and can, for example, be filled in capsules, moulded etc. Because of the self-dispersing ability of the compositions, non-lamellar particles form when contacted with GI-fluid. The polymeric solidifying agent is a preferably biotollerable polymer, preferably having a melting point between 35 and 100° C., more preferably 40-95° C. and most preferably 45-90° C. A particularly preferred polymeric agent is polyethylene glycol (PEG) with molar mass in the range of 950-35000, most preferably 1000 to 10,000. PEG 4000 is a highly preferred example.

Because the compositions of the present invention are self-dispersing, they do not need to be administered in the form of a dispersion and indeed do not need to have been previously dispersed before administration. The compositions may conveniently be administered as a bulk composition in solid or concentrated liquid form (e.g. as a powder, tablet, powder, solid (semi-solid) or liquid filled capsule), rather than as a dispersion, while maintaining the high transport efficiency associated with colloidal dispersions, which are then generated by dispersion in vivo in the body fluid. The bulk administration will thus fragment and disperse as a highly uniform distribution of micron and sub-micron particles which are efficiently transported to sites of action. Furthermore, the non-lamellar structure of the particles generated by this in vivo dispersion can provide control over active agent release and efficient targeting and delivery across biological membranes. In one embodiment, the compositions of the present invention are thus formulated to comprise at least 50% by weight of a pharmaceutical formulation with no more than 10% by weight being total organic solvent content (including any solvent present in the composition) and the remainder non-solvent formulating agents. The term "formulating agents" being used herein to indicate agents having no significant pharmaceutical effect in the quantities used but being pharmaceutically acceptable and useful in formulating the compositions of the invention into pharmaceuticals. Examples of such agents include excipients, encapsulants, coatings, colouring, flavouring, binding agents, pH adjusters, tonicity modifiesr and such like.

Active agents suitable for inclusion in the compositions of the present include human and veterinary drugs and vaccines, diagnostic agents, "alternative" active agents such as plant essential oils, extracts or aromas, cosmetic agents, nutrients, dietary supplements etc.

Examples of suitable drugs include antibacterial agents such β-lactams or macrocyclic peptide antibiotics, anti fungal agents such as polyene macrolides (e.g. amphotericin B) or azole antifungals, anticancer and/or anti viral drugs such as nucleoside analogues, paclitaxel, and derivatives thereof, anti inflammatorys, such as non-steroidal anti inflammatory drugs, cardiovascular drugs including cholesterol lowering and blood-pressure lowering agents, analgesics, antidepressants including serotonin uptake inhibitors, vaccines and bone modulators. Particularly suitable active agents include anaesthetics such as propofol, hormones and hormone derivatives such as testosterone and testosterone derivatives (e.g. testosterone undecanoate), anticancer agents such as paclitaxel and docetaxel; immunosuppressants such as cyclosporine, tacrolimus, or sirolimus and peptide active agents such somatostatin and analogues thereof (e.g. octreotide).

Diagnostic agents include radionuclide labelled compounds and contrast agents including X-ray, ultrasound and MRI contrast enhancing agents. Nutrients include vitamins, coenzymes, dietary supplements etc. The active agents for use in the present invention will generally not be any of components a), b) or c) as described herein.

It is a particular feature of the present invention that no high energy techniques are necessary in order to form dispersions of non-lamellar particles from the compositions of the invention. As a result, heat and/or shear sensitive active agents may be included where these might not be suitable for formulation in dispersed non-lamellar particles formable by previous methods.

In one embodiment, the compositions and particles of the invention thus include at least one temperature sensitive and/or shear sensitive active agent. Temperature sensitive active agents may be considered to be those in which exposure to temperatures of 70° C. or higher for 20 minutes or more, in aqueous conditions, result in the loss of at least 10% of the original biological activity. Peptides and proteins are the most common active agents which are temperature sensitive and thus these form preferred active agents for use in the invention, particularly in this embodiment. Shear sensitive active agents will typically be large and/or multi-subunit proteins which become disrupted by high shear conditions.

Preferred active agents thus include human and veterinary drugs selected from the group consisting of peptides such as adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, peptide T and its related peptides calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, fibronectin fragments and their related peptides, gastrointestinal peptides, growth hormone releasing peptides, immunostimulating peptides, insulins, insulin analogues and insulin-like growth factors, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides (e.g. octreotide), substance P and its related peptides, transforming growth factors (TGF) and their related peptides, tumour necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons, interleukins, leptins, leukemia inhibitory factors, stem cell factors, transforming growth factors and tumor necrosis factors; selected from the group consisting of antivirals, steroidal anti-inflammatory drugs (SAID), non-steroidal anti-inflammatory drugs (NSAID), antibiotic, antifungals, antivirals, vitamins, hormones, retinoic acid and retinoic acid derivatives (including tretinoin), prostaglandins, prostacyclins, anticancer drugs, antimetabolic drugs, miotics, cholinergics, adrenergic antagonists, anticonvulsants, antianxiety agents, tranquilizers, antidepressants, anaesthetics, analgesics, anabolic steroids, estrogens, progesterones, glycosaminoglycans, polynucleotides, immunosuppressants (e.g. tacrolimus and sirolimus) and immunostimulants, cardiovascular drugs including lipid lowering agents and blood-pressure lowering agents, bone modulators; vaccines, vaccine adjuvants, immunoglobulins and antisera; diagnostic agents; cosmetic agents, sunscreens and self-tanning agents; nutrients; dietary supplements; herbicides, pesticides, and repellents. Further examples of active agents can be found for instance in Martindale, The Extra Pharmacopoeia.

The aqueous fluid referred to herein for contacting with the compositions of the present invention may be water or may be any other suitable aqueous solution or mixture including, for example, pharmaceutically acceptable carrier solutions. Suitable solutions include buffers and isotonic solutions for injection e.g. 0.9% saline at around physiological pH. These fluids are highly suitable for preparing a dispersion at the point of care and may be included in the kit of the invention.

In one preferred embodiment, the fluid may be a body fluid such as blood or gastro-intestinal (GI) fluid. In this embodiment, the composition is administered as a lipid/active agent mixture, optionally with a cosolvent or a polymeric agent to render this liquid or solid (semi-solid) or improve the viscosity properties. Suitable co-solvents are discussed herein above.

In a preferred embodiment of the invention, the particles of the invention (which as referred to herein include the particles formed and formable by the method of the invention) are essentially stable both in terms of phase behaviour and particle size distribution to storage for at least 10 days at 4° C. and/or at room temperature. This is a considerable advantage over previously known dispersions of non-lamellar particles (requiring high energy fragmentation or hydrotropes) since these known dispersions are typically not stable to storage for more than a short period (e.g. a few days—see for example Kamo, supra). It is preferred that the amphiphile particles of the invention are stable to storage for at least 1 or 2 months, preferably at least 3 months and more preferably at least 6 months at both 4° C. and room temperature.

It is a particular advantage that the particles and dispersions of the invention are stable to storage at 4° C. because this is the typical refrigerated storage condition practiced and recommended for many biologically active agents and preparations. Previously known non-lamellar (especially reversed hexagonal) particles are even less stable at 4° C. than they are at room temperature and are thus unsuitable for generating formulations for refrigerated storage. In particular, previously known glycerol monooleate (GMO) based non-lamellar dispersions are generally unstable at 4° C.

A particle size distribution can be considered essentially stable to storage if the average (mean) particle size increases no more than two fold during the storage period. Preferably, the average size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period. In a highly preferred embodiment, particle size distribution of the compositions of the invention alter in average particle size and particle size distribution width at half-height by no more than 10% and remain monomodal on storage for the periods indicated above.

It is particularly important in the case of colloidal dispersions for use in intravenous or intra-arterial administration that the particle size distribution be stable to storage. A composition containing even a relatively small component of non-colloidal particles may cause embolism, or at least unpredictable rates of release upon administration directly to the blood stream. Similarly, the controlled release of an active agent may be dependent upon a reliable particle size distribution in a composition for administration by any other route. Pharmaceutical, diagnostic and veterinary products are also desirably stable to storage for several months or the cost and availability of the product is significantly adversely affected. The invention thus significantly improves the prospect of an active agent formulated in a dispersion of non-lamellar particles forming a safe and available product.

It is additionally important that the phase structure of the particles in dispersion remains stable to storage so that the rate of release of any active agent may be effectively predicted. In a preferred embodiment, the particles of the invention remain non-lamellar upon storage for the periods discussed above. By "remains non-lamellar" is indicated that no more than 10% of the non-lamellar particles should adopt a lamellar or micellar phase structure upon storage, preferably no more than 5% and more preferably no more than 2%. In some cases the proportion of non-lamellar particles may even increase upon storage.

The dispersions formed or formable from the compositions of the present invention are further remarkable in that they can both form and stably remain as dispersions in aqueous fluids at surprisingly high lipid concentrations. Typically, non-lamellar lipid dispersions are formed and remain stable, if at all, at very low total amphiphile concentrations. The maximum typical concentration is frequently 1-2% by weight amphiphile in water with 5-6% being an unusually high concentration. In contrast, the dispersions of and formed by the present invention may be stable in aqueous fluids at concentrations of up to 10 wt %, preferably up to 15 wt % and more preferably up to 20% total amphiphile in water. By "stable" is meant stable in both particle size and phase behaviour, as discussed herein.

In a preferred embodiment of the present invention, the monoacyl lipid a) may comprise or consist of components which, in pure form, generate a micellar or preferably lamellar phase upon contact with water. The most commonly used monoacyl lipid for the formation of bulk or dispersed non-lamellar phases is glycerol monooleate (GMO). This monoacyl lipid may be used in the compositions of the present invention but is not suitable for this embodiment because it forms a cubic liquid crystalline phase when the pure compound is exposed to water.

The amphiphile particles of the present invention are non-lamellar and are formed or formable by self-dispersion of the compositions of the invention. Following formation of such particles, however, the dispersion may be further treated in a number of ways, depending upon desired application.

In one embodiment of the invention, the particles formed or formable from the composition of the invention may be concentrated and/or dried and/or co-melted with suitable polymeric agents to provide a concentrated dispersion, a "dry" powder or a solid (semi-solid e.g. gel or waxy solid) matrix. Suitable techniques for concentration, drying and preparation of a solid (semi-solid) include ultrafiltration, solvent evaporation, freeze drying, spray drying and co-melting of the amphiphile components with a polymeric agent (e.g. polyethylene glycol (PEG)) or other suitable agent followed by cooling to form a solid (semi-solid) precursor.

Where "dry" powders are generated, these may be completely or essentially free of aqueous solvent or may continue to contain some solvent as part of the structured core of the particles. Where all or most of the aqueous solvent is removed, the resultant particles may lose their non-lamellar structure but this will be regenerated upon contact with an aqueous fluid. Such powders are capable of regenerating amphiphile particles of the invention and thus form a further aspect thereof. Drying may preferably be conducted in the presence of at least one protective agent and/or at least one agent for aiding resuspension of the resulting powder. Suitable agents are well known and include sugars and hydrophilic polymers such as polyvinyl pyrollidone or polyethylene glycol.

The powders generated from the compositions of the present invention are in themselves compositions of the invention because they comprise amphiphile mixtures that are "capable of self-dispersion". In use, a micronised dried powder may not be required to self-disperse because this dispersion may already be carried out prior to or during the drying process. In such a powder, the particles may be present individually, for example within a matrix of a substance such as trehalose. The amphiphile mixtures forming the particles are, however, inherently capable of dispersing with out high energy fragmentation and without the need for hydrotropes and so are compositions of the invention. This is in contrast to known powder compositions which must be generated by use of high energies and/or hydrotopes and comprise amphiphile compositions which are incapable of self dispersion. The powder precursors generated from the compositions of the present invention are highly suitable for nasal administration by inhalation of the powder. Such a powder may also optionally be mixed with carrier or excipient powders as necessary.

The compositions, (e.g. solid and/or semi-solid or liquid compositions with or without a cosolvent), dispersions, particles and/or dried materials of the invention may be formulated in any suitable form for delivery to a patient. This includes pre-formulated dispersions (e.g. in sterile containers ready for administration) and concentrated dispersions for dilution before use, powders for suspension or direct administration (e.g. by inhalation), powder, solid (semi-solid) or liquid filled capsules, tablets, coated tablets, suppositories, gels, creams, ointments and other topical compositions such as eye drops, sprays (such as skin, mouth or nasal sprays e.g. pump-sprays or aerosol sprays), wipes, patches, pastes and mouth washes. Suitable carriers and excipients for use in such formulations are well known in the relevant art.

The compositions of the invention are also suitable as carriers for non-pharmaceutical agents such as essential oils, perfumes, aromas etc. Suitable formulations and applications for these are also well known and include cosmetic and household applications including skin treatments (either alone or when formulated with at least one cosmetic active agent, perfume etc.), personal cleaners/cleansers such as skin, nail, face, or mouth cleansers, absorbers for internal or external toxins such as balms, and detoxifying suspensions, household or personal washing powders/liquids, bath/shower gels, cleaning liquids, sprays, gels or foams and bath oils.

A further preferred processing step which may be carried out on the amphiphile particles formed or formable by self-dispersion of the compositions of the invention is a heat treatment step. In this, a dispersion of amphiphile particles is heated to a temperature in the range of around 75 to 200° C., preferably 90 to 140° C. for between 1 minute and 4 hours, generally between 10 minutes and 1 hour and subsequently cooled to room temperature. The effects of this heat treatment step are several but they include the conversion of an even greater proportion of particles to non-lamellar phase and/or the narrowing of the particle size distribution. The heat treatment may also improve the storage stability of the particles in dispersion, both in terms of their phase behaviour and their particle size distribution.

The heat treatment step described above may also be used to enhance the loading of active agents into self dispersed particles of the invention. In this embodiment, the active agent should be heat tolerant and is dissolved in the aqueous medium in which the particles are dispersed. The dispersion is then heat treated as described above and the active agent is thereby incorporated into the particles. These particles are highly stable and may thereafter be processed by any suitable method, including those described herein, into any appropriate formulation.

Active agents which are suitable for any embodiment of the invention but are particularly suited for loading by heat treatment include steroids, sparingly soluble weakly basic drugs, fibrins, statins, dipins, and azoles. Specific preferred examples of these include progesterone, testosterone, simvastatin, lovastatin, nifedipin, felodipin, nicardipin, nimodipin, itraconazole, fluconazole, miconazole, econazole, voriconazole, clotrimazole, ketoconazole, fulvestrant, fenofibrate, octreotide, undecanoate, estradiol, cortisone, hydrocortisone, 11a-hydroxyprogesterone, clofibrate gemfibrozil, bezafibrate, ciprofibrate.

The amphiphile based particles of the invention (including those formed or formable from the compositions of the invention) may desirably also be modified with surface active agent (especially a polymer) e.g. a starch or starch derivative, a copolymer containing alkylene oxide residues (such as ethylene oxide/propylene oxide block copolymers), cellulose derivatives (e.g. hydroxypropylmethylcellulose, hydroxyethylcellulose, ethylhydroxyethylcellulose, carboxymethylcellulose, etc) or graft hydrophobically modified derivatives thereof, acacia gum, hydrophobically modified polyacrylic acids or polyacrylates, etc. The surface active polymer may also be used to provide a functional effect on the surface of the particles, for example, in order to selectively bind or target the particles to their desired site of action. In particular, polymers such as polyacrylic acids, hyaluronic acids or chitosans may be used to provide mucus adhesive particles. Such particles will thus tend to remain localised, thus increasing the spatial control over the active agent release. Compositions of the invention comprising such surface modified particles form a further embodiment of the invention.

One additional and surprising advantage of the particles of and formed by the present invention is that they serve to increase the transport of active agents across biological barriers such as the blood-brain barrier and/or the walls of the GIT. The present invention thus also provides a method for increasing the bioavailability of an orally administrable active agent and/or increasing the effectiveness of an active agent having a site of action in the brain. This method comprises formulating the appropriate active agent(s) in compositions, dispersions and/or particles of the present invention and thereafter administering these to the subject. The present invention can provide compositions with enhanced blood/brain barrier crossing properties (see Example 17) and increased oral bioavailability of at least 5 times, preferably at least 10 times the oral bioavailability of the active agent in saline solution (see Example 20). Moreover it can provide increased bioavailibility of (especially sparingly soluble) active substances even when compared to (commercially available) reference products (see Example 18). Evidently, such increased bioavailability over existing commercial preparations offers considerable advantages.

Many active agents including those discussed herein are administrable orally and/or could be administered orally by means of the present invention. Examples of active agents having a site of action in the brain include anti-infective agents for treating brain infections (e.g. anti-fungal and/or anti-bacterial antibiotics) and drugs acting directly on the nervous system including analgesics (especially opioid/narcotic analgesics), anaesthetics, mood controlling agents such as antidepressants, and treatments for brain disorders such as Parkinson's disease (e.g. dopamine analogues), Creutzfeldt-Jakob Disease, Alzheimer's disease and cancers to the brain (e.g. anti-cancer agents such as taxol derivatives). The use of the compositions of the invention (with appropriate active agents) in the treatment of conditions such as any of pain, depression, brain disorders or brain cancers/tumours and their use in the manufacture of medicaments for the treatment of such conditions thus form further aspects of the invention.

The compositions of the present invention are highly effective in the delivery of active agents, especially pharmaceutical agents such as drugs, and diagnostic agents. In further aspects, the invention thus provides methods to solubilize, encapsulate, protect and/or stabilize at least one active agent, said method comprising formulating the active agent as a composition as described herein. All of these methods provide improvements in their respective parameter(s) relative to the same active agent prepared as a formulation in the absence of the compositions of the present invention. Typically this comparative formulation will be the standard pharmaceutical formulation for that active.

The compositions of the present invention are also highly effective in delivering active agents to subjects in vivo. In particular, the compositions may serve to enhance the effect of an active agent by ensuring that a greater proportion of the administered dose takes effect at the site of action relative to other formulations. In a further aspect, the invention thus provides a method to increase the uptake, permeation, transport, circulation time, duration of action, efficacy, therapeutic index, bioavailability, patient convenience and/or patient compliance, for a pharmaceutically active agent, said method comprising administering said active agent as a composition or formulation of the present invention, as described herein. Such methods will generally allow a reduced dose of active agent to be used, or allow a particular dose to be administered with a lower frequency or higher efficacy. In addition, even where a similar dose or dosing regime is applied, the compositions of the invention may continue to have advantages. In further aspects, the invention thus also provides methods to provide a more therapeutic pharmacokinetic profile, decreased level of excipients, and/or improved safety profile for a pharmaceutically active agent, said methods comprising formulating and/or administering said active agent as a formulation as herein described.

The present invention will now be illustrated by reference to the following non-limiting examples and the attached Figures, in which.

EXAMPLES

Example 1

Identifying Non-lamellar Phase Regions

Figure 1:
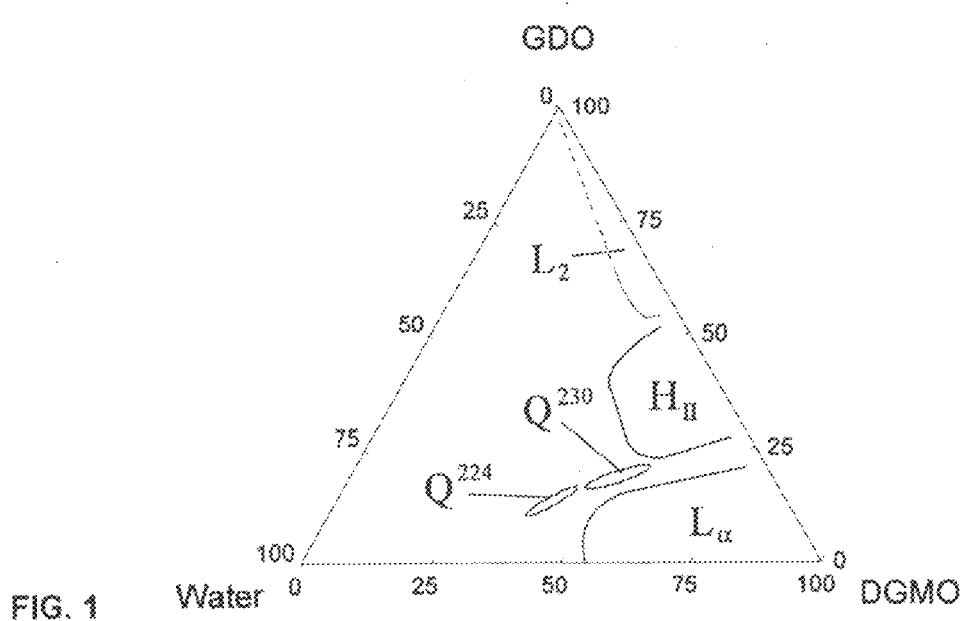
FIG. 1 shows the phase diagram of the ternary mixture DGMO/GDO/water at 25° C.

The phase behavior of the ternary system DGMO/GDO/water (DGMO; Diglycerol Monooleate; RYLO™ PG 29, and GDO; Glycerol Dioleate; EMUSIFIER TS-PH 008; DANISCO, Denmark) was determined using small angle x-ray scattering (SAXS) combined with observations between crossed polarizers. Samples were prepared by mixing the lipid components in the correct proportions into small glass vials and thereafter adding water (typical sample weights were 1 g). The vials were immediately sealed and the samples were equilibrated by repeated centrifugation and thereafter stored for at least 2 weeks before the SAXS measurements. The results are collected in the phase diagram shown in FIG. 1. This figure displays 3 non-lamellar liquid crystalline (lc) phase regions: The reversed hexagonal phase ($H_{II}$) and the two bicontinuous cubic phases $Q^{224}$ and $Q^{230}$. A further non-lamellar phase was identified as the liquid reversed micellar $L_2$ phase. At DGMO contents above 75% (weight percent with respect to GDO), a lamellar phase ($L_\alpha$) is formed. The $H_{II}$ phase exists at weight ratios of DGMO/GDO between approximately 65/35 and 40/60 and at water contents equal to or greater than 5 wt %. Importantly, the non-lamellar $H_{II}$ phase and the non-lamellar cubic $Q^{224}$ phase coexist with a dilute water phase in the water corner of the phase diagram. This behavior is commonly necessary for the formation of dispersions of non-lamellar lc phase particles.

Example 2

Non-lamellar Reversed Phase Nanoparticles 2.1—Preparation of a Non-Lamellar Dispersion A dispersion of non-lamellar (>70% by weight of amphiphile) and lamellar (<30% by weight of amphiphile) particles was formed by mixing 0.60 g of DGMO and 0.40 g of GDO. The components were molecularly mixed by heating for 5 min at 70° C. and vortexing. The homogenous lipid melt (0.80 g) was added drop wise to a solution containing 0.08 g of Pluronic® F127 (BASF, U.S.A) in 39.2 g of deionized water. The resulting coarse dispersion was put on a shaking table (350 rpm) and shaken for 12 hours to give a white homogenous dispersion.

Figure 2:
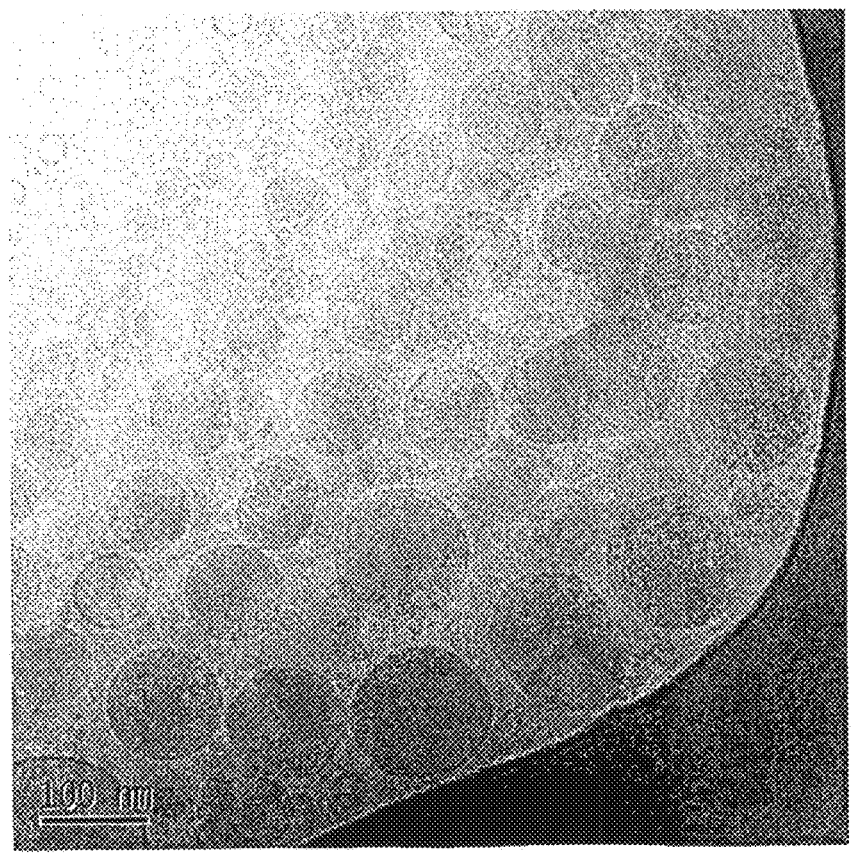
FIG. 2 shows a cryo-transmission electron micrograph of a self-dispersed sample of DGMO/GDO/Pluronic® F127.

The particle size was measured using laser diffraction (Coulter LS230). The size distribution was found to be narrow and monomodal. A cryo-TEM image of the dispersion is shown in FIG. 2 and particles with dense (dark) inner structures of reversed liquid crystalline phase can be observed together with some lamellar particles (vesicles).

2.2—Heat Treatment

An optional cycle of heat treatment was carried out on the dispersion prepared in Example 2.1.

Figure 3:
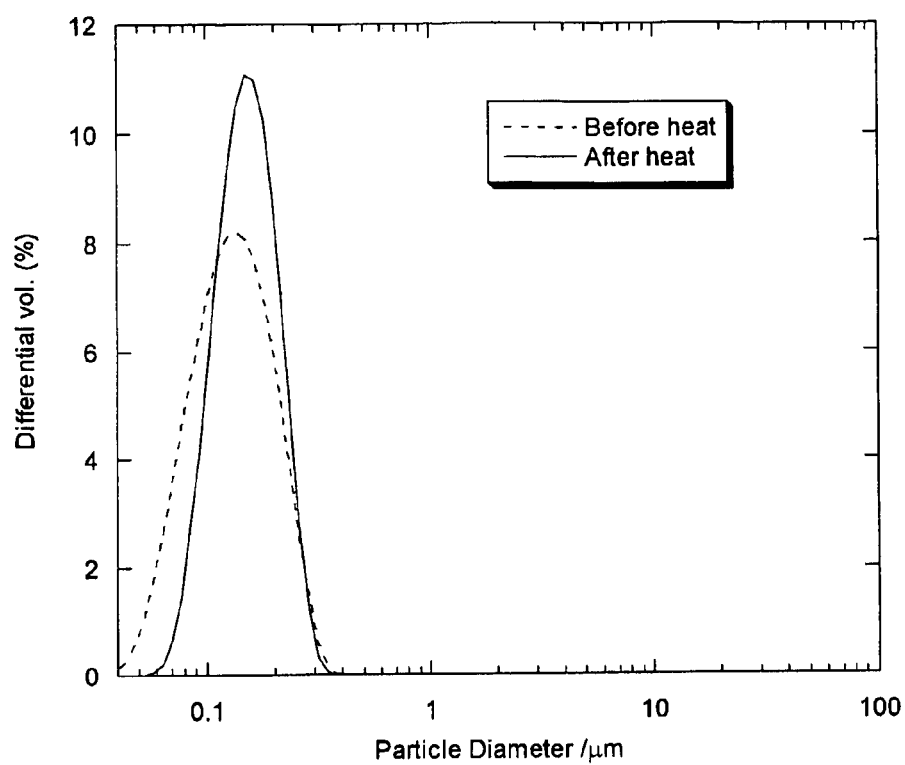
FIG. 3 shows the particle size distributions of a self-dispersed DGMO/GDO/Pluronic® F127 sample before and after heat treatment.

A sample of the dispersion generated in Example 2.1 (25 mL) was autoclaved (125° C., 20 min) and cooled to room temperature. The particle size distribution was narrowed and when examined by cryo-TEM, a still greater proportion of the particles showed non-lamellar character (internal reversed hexagonal phase). The particle size distribution before and after heat treatment is shown in FIG. 3.

Components:

a DGMO b GDO c Pluronic® F127

| Formulation | a:b:c | abc wt % | medium | Aq wt % | Phase before | Temp ° C. | Time min | Phase after |
|---|---|---|---|---|---|---|---|---|
| I | 54.5:36.4:9.1 | 2.2 | deionized water | 97.8 | Rev. hex./lam* | 125 | 20 | rev. hex.** |

*rev. hex./lam = mixed reversed hexagonal (>70% by weight of amphiphile) and lamellar (<30% by weight of amphiphile) particles
**rev. hex. = reversed hexagonal particles (>90% by weight of amphiphile)

Example 3

Further Composition

The effect of adding another stabilizing agent was considered by preparing a second composition by the method of Example 2.1. DGMO (1.40 g), GDO (1.15 g) and Polysorbate 80 (P80; Apoteket, Sweden) (0.46 g) were molecularly mixed by heating for 5 min at 70° C. and vortexing. The homogenous lipid melt (2.0 g) was added drop wise to 38.0 g of deionized water. The resulting coarse dispersion was put on a shaking table and shaken for 12 hours to give a white homogenous dispersion.

Figure 4:
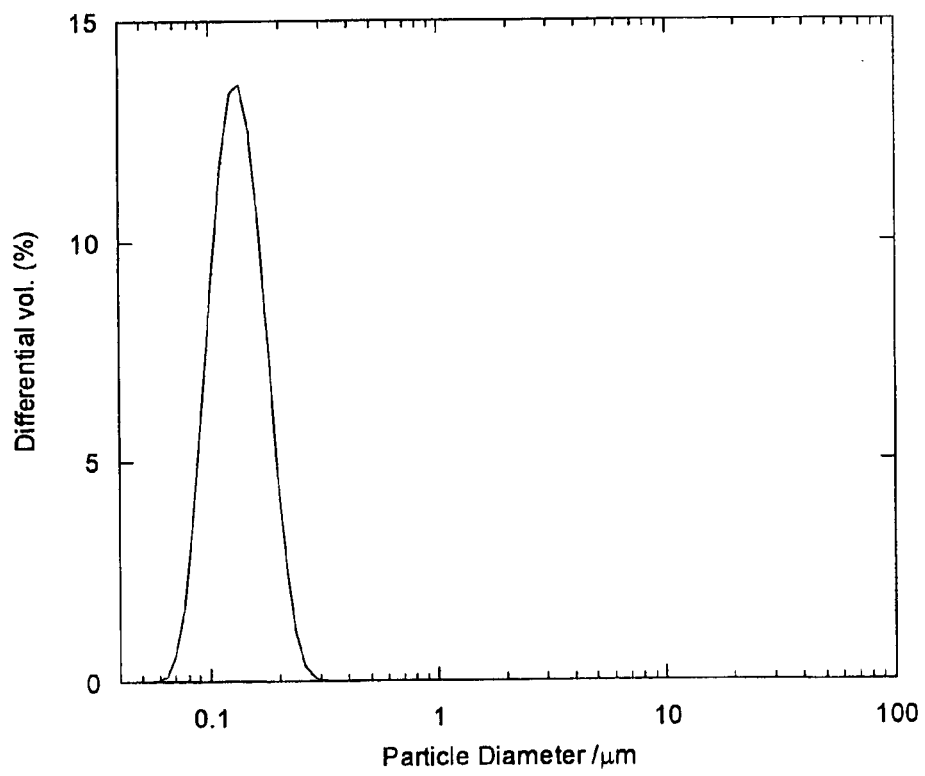
FIG. 4 shows the particle size distributions of a self-dispersed DGMO/GDO/Polysorbate 80 sample.

The particle size was measured using laser diffraction (Coulter LS230). The size distribution was found to be narrow and monomodal as indicated in FIG. 4.

Components:

a DGMO b GDO c Polysorbate 80

| Formulation | a:b:c | abc wt % | Medium | Aq wt % | Phase after shaking |
|---|---|---|---|---|---|
| II | 46.5:38.2:15.3 | 5 | deionized water | 95 | non-lamellar* |

*non-lamellar = particles with disordered inner structure consisting of multiply connected bilayers (>90% by weight of amphiphile).

Example 4

Further Composition

Figure 5:
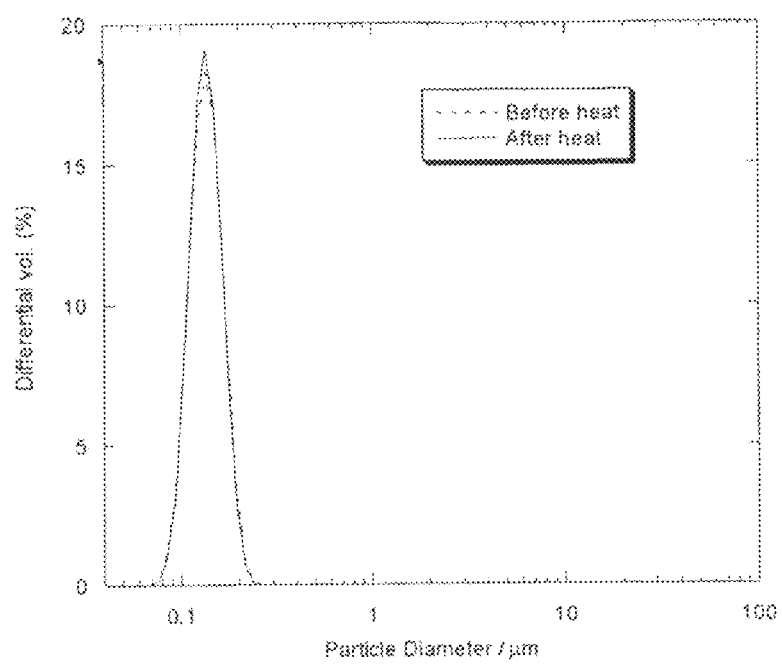
FIG. 5 shows the particle size distributions of a self-dispersed DGMO/GDO/Polysorbate 80 sample before and after heat treatment.
Figure 6A:
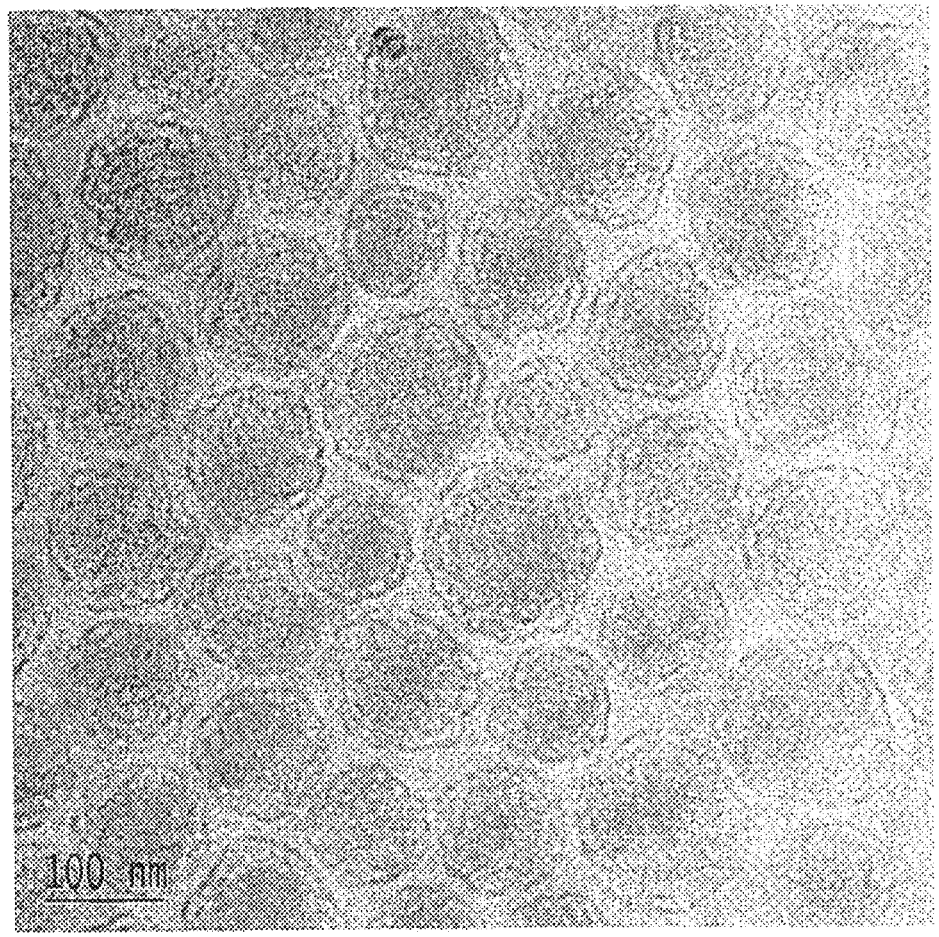
FIG. 6 shows cryo-transmission electron micrographs of a self-dispersed sample of DGMO/GDO/Polysorbate 80 after heat treatment.
Figure 6B:
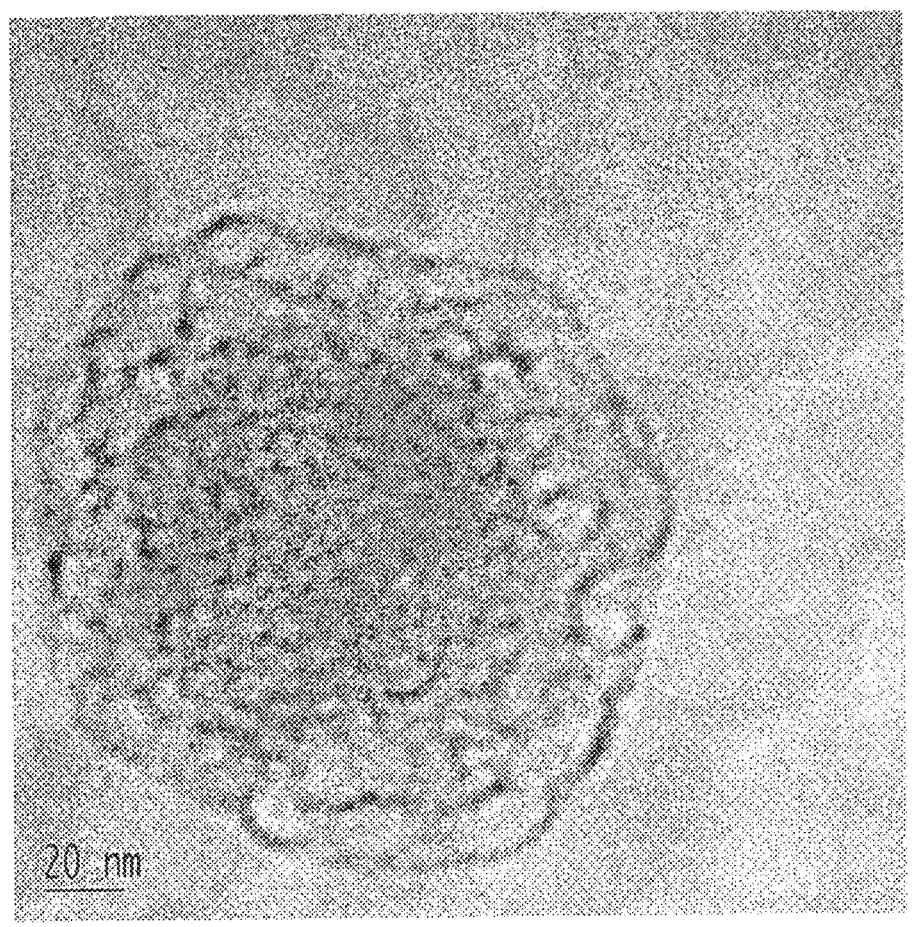

A dispersion consisting of DGMO (2.125 g), GDO (2.125 g) and P80 (0.75 g) in 95.0 g of deionized water was prepared according to the methods of Examples 2.1 and 2.2. The size distributions obtained before and after heat treatment were both narrow and monomodal as indicated in FIG. 5. The heat treated sample was investigated using cryo-TEM. Cryo-TEM images are shown in FIGS. 6a and 6b and clearly evidence the formation of non-lamellar nanoparticles of uniform size containing a disordered inner structure of multiply connected bilayers.

Figure 8:
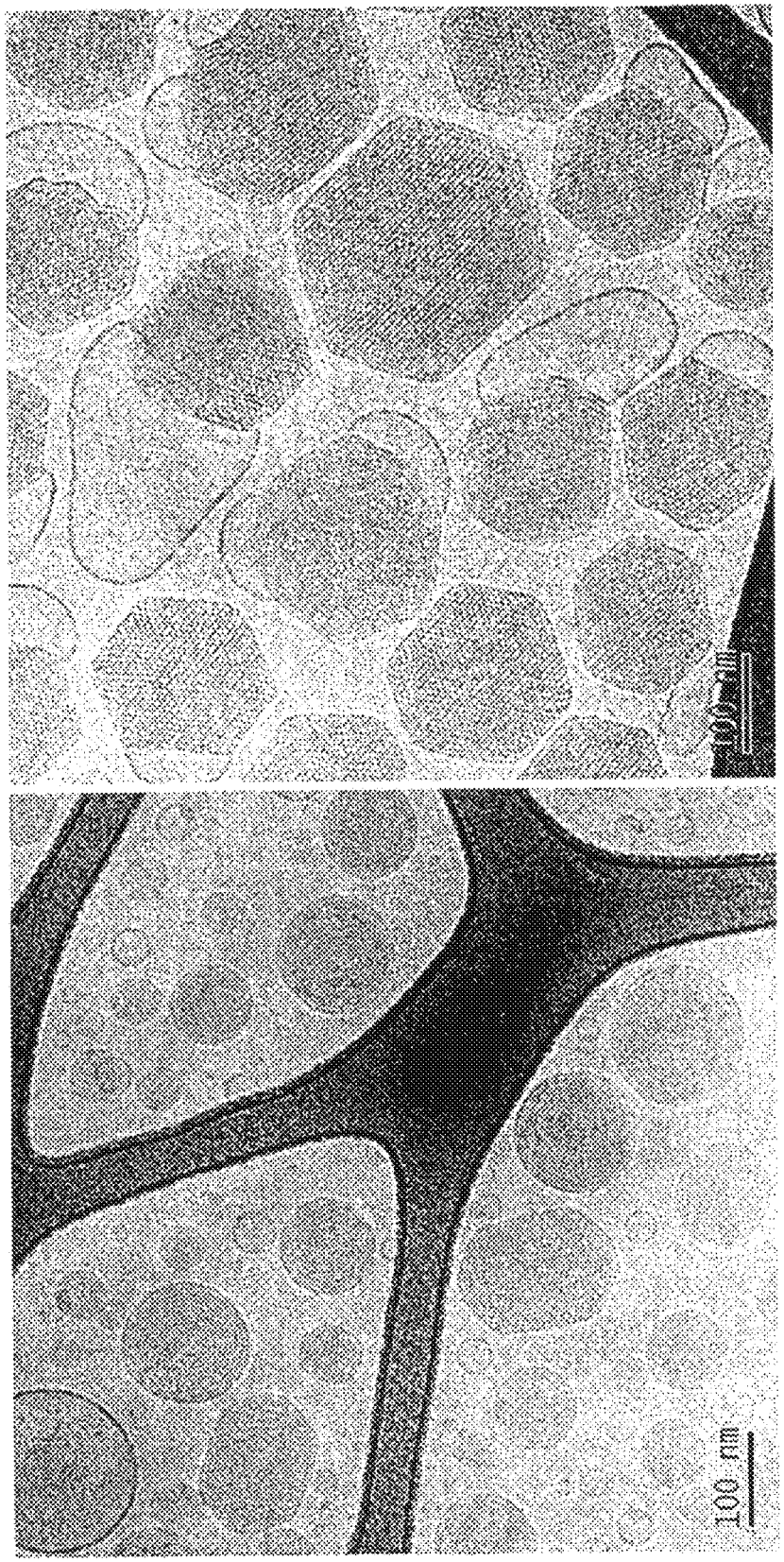
FIG. 8 shows cryo-transmission electron micrographs of a self-dispersed sample of DGMO/GDO/OA/Pluronic® F127 before and after heat treatment.

Components:
a DGMO
b GDO
c Polysorbate 80 cryo-TEM. Cryo-TEM images obtained from the sample before and after heat treatment are shown in FIG. 8. The reversed hexagonal structure is clearly observed within the particles in the cryo-TEM images and Fast Fourier Transforms (FFTs) of the internal structure indicate a hexagonal spacing of about 58 Å (±5 Å) [5.8 nm (±0.5 nm)].

Components:
a1 DGMO
a2 OA
b GDO
c Pluronic® F127

| Formulation | a:b:c | abc wt % | medium | Aq Phase wt % | before | Temp ° C. | Time min | Phase after |
|---|---|---|---|---|---|---|---|---|
| III | 42.5/42.5/15.0 | 5 | deionized water | 95 | non-lam.* | 125 | 20 | non-lam.* |

*non-lam. = non-lamellar particles with disordered inner structure consisting of multiply connected bilayers (>90% by weight of amphiphile).

This particular composition is also well suited for preparing a liquid precursor of the non-lamellar phase dispersion.

| Formulation | a1:a2:b:c | a1a2bc wt % | medium | Aq Phase wt % | before | Temp ° C. | Time min | Phase After |
|---|---|---|---|---|---|---|---|---|
| IV | 52.6:2.3:35.3:9.8 | 5.4 | deionized water | 94.6 | rev. hex./lam* | 125 | 20 | rev. hex.** |

*rev. hex./lam = mixed reversed hexagonal (>70% by weight of amphiphile) and lamellar (<30% by weight of amphiphile) particles
**rev. hex. = reversed hexagonal particles (>90% by weight of amphiphile)

The same components were used in the same ratios. The components were molecularly mixed by heating to 40° C. for 15 min and vortexing. The liquid formulation was then dispersed into water (5 wt % amphiphile) with gentle shaking resulting in a milky white dispersion of non-lamellar phase particles. The liquid precursor formulation was also fortified with 10% by weight of a co-solvent (e.g. ethanol, N-methyl-2-pyrrolidone (NMP), propylene glycol, PEG400, glycerol) and thereafter dispersed into water (5 wt % amphiphile) with gentle shaking resulting in a milky white dispersion of non-lamellar lc phase particles.

Example 5

Further Composition: Including Anionic Component (Fatty Acid)

Figure 7:
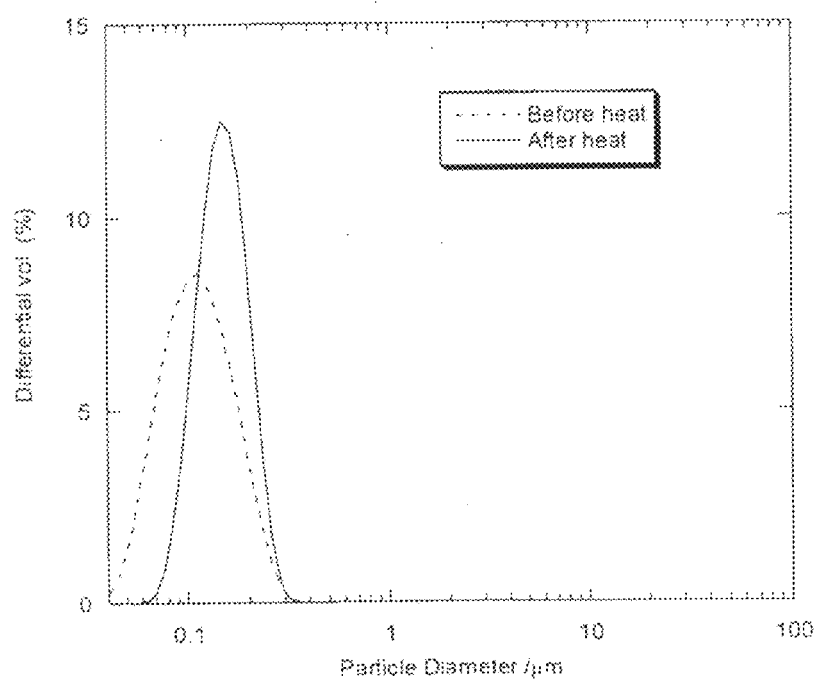
FIG. 7 shows the particle size distributions of a self-dispersed DGMO/GDO/OA/Pluronic® F127 sample before and after heat treatment.

A dispersion consisting of DGMO (2.98 g), GDO (2.0 g), Oleic Acid (OA; Apoteket, Sweden) (0.13 g) and Pluronic® F127 (0.553 g) in 100.0 g of deionized water was prepared according to the methods of Examples 2.1 and 2.2. The size distributions obtained before and after heat treatment were both monomodal but the heat treated sample displayed a narrower distribution as indicated in FIG. 7. The heat treatment was also accompanied by an increased proportion of particles with non-lamellar character as was evidenced by

Example 6

Further Composition: Including Anionic Phospholipids

Figure 9:
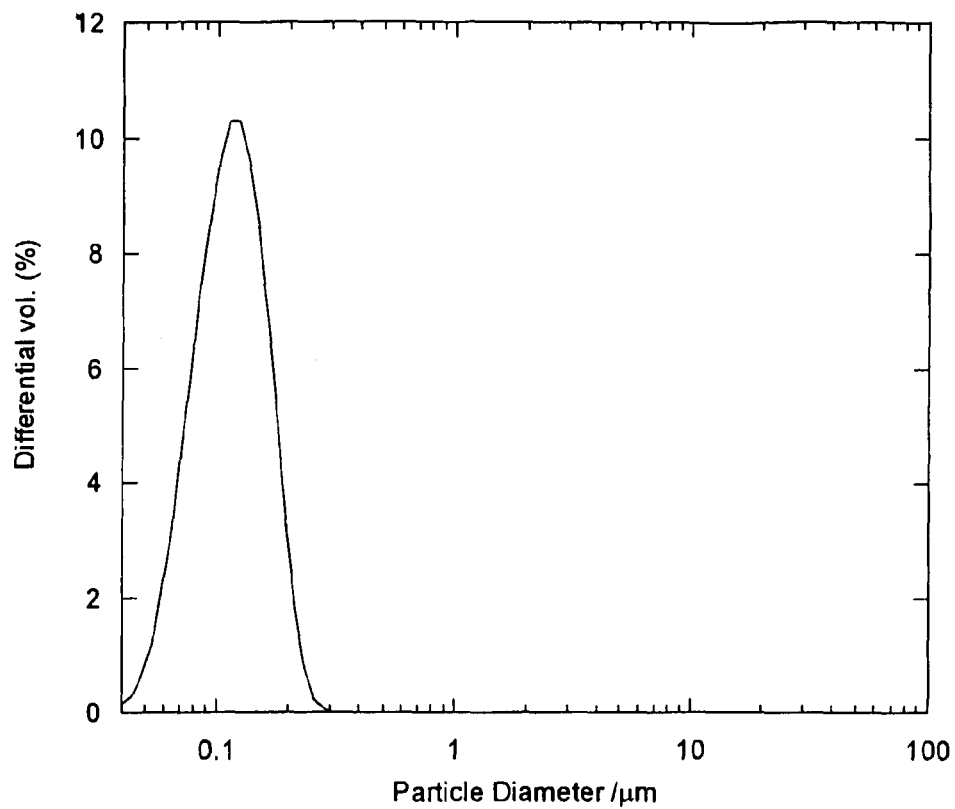
FIG. 9 shows the particle size distribution of a self-dispersed DGMO/GDO/DOPG/Pluronic® F127 sample.

A dispersion consisting of DGMO (0.150 g), GDO (0.100 g), DOPG (Dioleoyl Phosphatidylglycerol; Avanti Polar Lipids, U.S.A) (0.007 g) and Pluronic® F127 (0.0282 g) in 4.75 g of deionized water was prepared according to the method of Example 2.1. The size distribution obtained after shaking was narrow and mono-modal as indicated in FIG. 9.

Components:
a1 DGMO
a2 OA
b GDO
c Pluronic® F127

| Formulation | a1:a2:b:c | a1a2bc wt % | Medium | aq wt % | Phase after shaking |
|---|---|---|---|---|---|
| V | 52.6:2.5:35.0:9.9 | 5.7 | deionized water | 94.3 | rev. hex./lam* |

*rev. hex./lam = mixed reversed hexagonal (>70% by weight of amphiphile) and lamellar (<30% by weight of amphiphile) particles

Example 7

Further Composition

Figure 10:
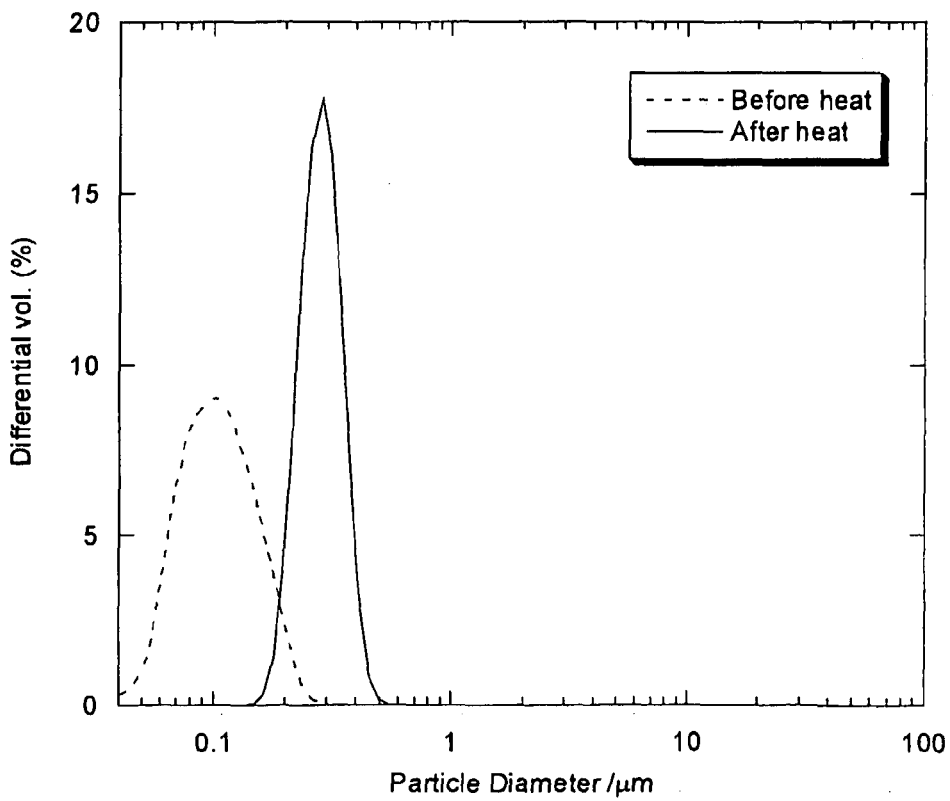
FIG. 10 shows the particle size distributions of a self-dispersed DGML/GDO/Pluronic® F127 sample before and after heat treatment.

A dispersion consisting of DGML (Diglycerol Monolinoleate; EMULSIFIER TS-PH 038; DANISCO, Denmark) (1.50 g), GDO (1.00 g) and Pluronic® F127 (0.277 g) in 47.5 g of deionized water was prepared according to the methods of Examples 2.1 and 2.2. The size distributions obtained before and after heat treatment were both mono-modal but the heat treated sample contained larger particles and displayed a narrower distribution as indicated in FIG. 10. The heat treatment was also accompanied by an increased proportion of particles with non-lamellar character as was evidenced by cryo-TEM.

Components:
a DGML
b GDO
c Pluronic® F127

| Formulation | a:b:c | abc wt % | Medium | aq wt % | Phase before | Temp °C | Time min | Phase after |
|---|---|---|---|---|---|---|---|---|
| VI | 54.0:36.0:10.0 | 5.5 | Deionized water | 94.5 | rev. hex./lam* | 125 | 20 | rev. hex.** |

*rev. hex./lam = mixed reversed hexagonal (>70% by weight of amphiphile) and lamellar (<30% by weight of amphiphile) particles
**rev. hex. = reversed hexagonal particles (>95% by weight of amphiphile)

Example 8

Further Composition

Figure 11:
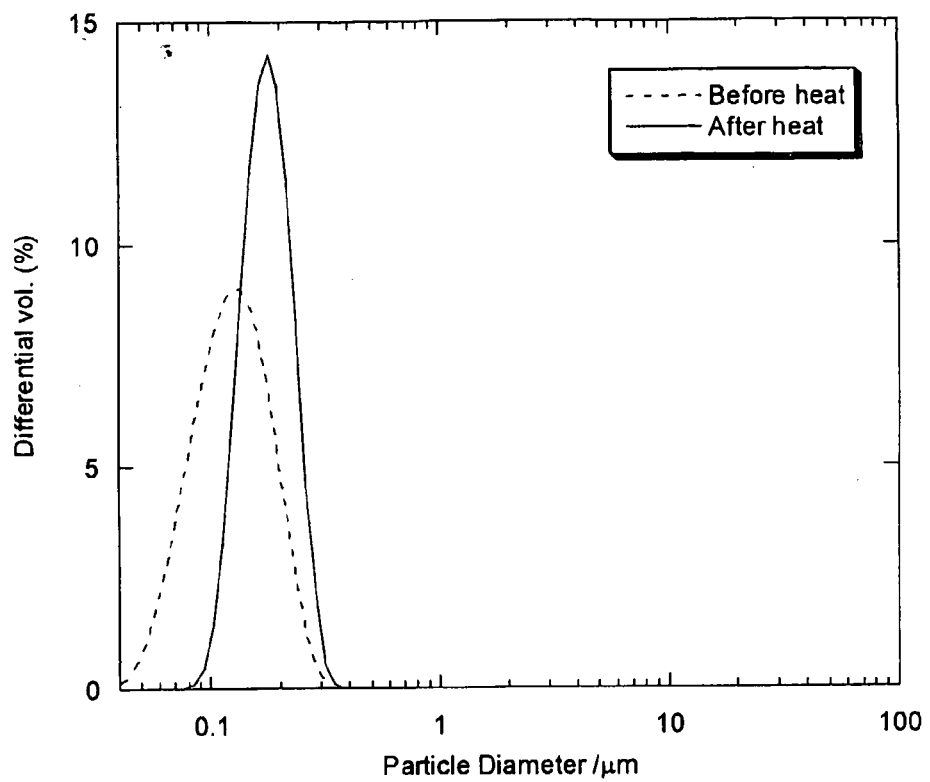
FIG. 11 shows the particle size distributions of a self-dispersed DGMO/GDO/GO-460V sample before and after heat treatment.

A dispersion consisting of DGMO (1.50 g), GDO (1.0 g) and GO-460V (PEG-60-sorbitol tetraoleate; Nikko Chemicals, Japan) (0.361 g) in 47.5 g of deionized water was prepared according to the methods of Examples 2.1 and 2.2. The size distributions obtained before and after heat treatment were both mono-modal but the heat treated sample displayed a narrower distribution as indicated in FIG. 11.

Components:
a DGMO
b GDO
c GO-460V

| Formulation | a:b:c | abc wt % | medium | aq wt % | Phase before | Temp °C | Time min | Phase after |
|---|---|---|---|---|---|---|---|---|
| VII | 52.4:35.0:12.6 | 5.7 | deionized water | 94.3 | rev. hex./lam* | 125 | 20 | rev. hex.** |

*rev. hex./lam = mixed reversed hexagonal (>80% by weight of amphiphile) and lamellar (<20% by weight of amphiphile) particles
**rev. hex. = reversed hexagonal particles (>95% by weight of amphiphile)

This particular composition is also well suited for preparing a liquid precursor of the reversed hexagonal phase dispersion. The same components were used in the same ratios with the addition of 10% by weight of a co-solvent (e.g. ethanol, N-methyl-2-pyrrolidone (NMP), propylene glycol, PEG400, glycerol). The liquid formulation was then dispersed into water (5 wt % amphiphile) with gentle shaking resulting in a milky white dispersion of mainly reversed hexagonal phase particles.

Example 9

Preparation of Highly Concentrated and Stable Non-lamellar Dispersion

Figure 12:
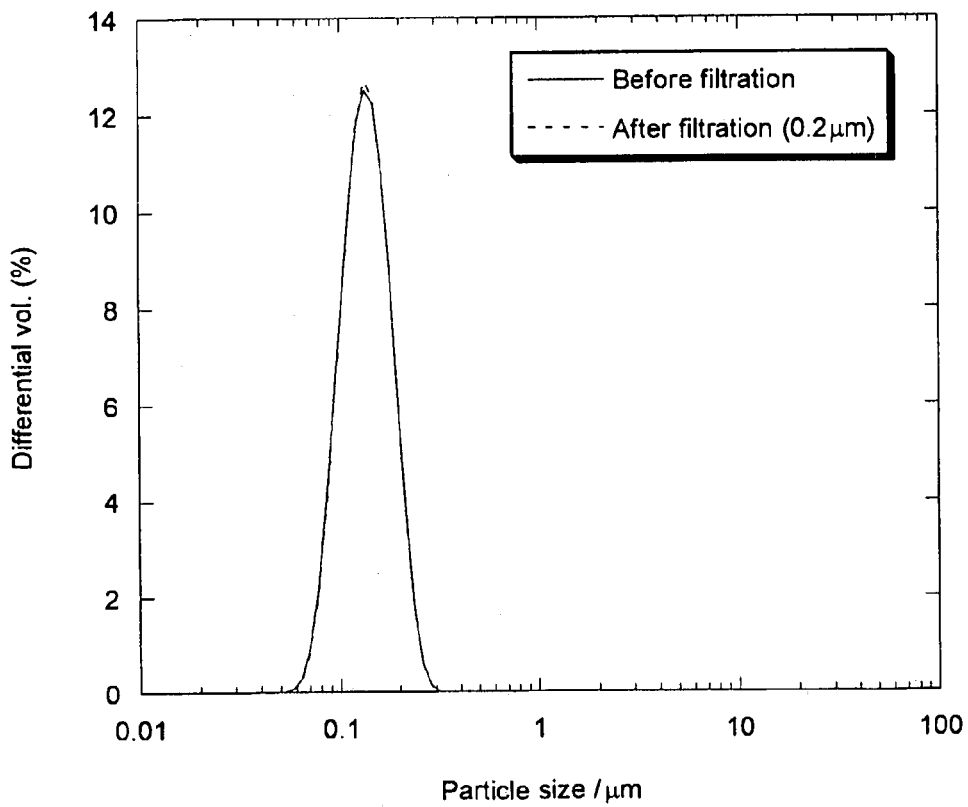
FIG. 12 shows the particle size distributions of a concentrated (20 wt %) self-dispersed DGMO/GDO/Polysorbate 80 sample before and after filtration.

A dispersion consisting of DGMO (2.55 g), GDO (2.55 g) and P80 (0.9 g) in 24.0 g of deionized water was prepared according to the method of Example 2.1. The obtained homogenous milky white dispersion was filtered through a 0.2 μm filter. The size distributions obtained before and after filtration were both narrow and monomodal as indicated in FIG. 12. The concentrated non-lamellar phase dispersion was found to be stable to storage at room temperature for at least 2 months.

Components:
a DGMO
b GDO
c Polysorbate 80

| Formulation | a:b:c | abc wt % | Medium | Aq wt % | Phase after shaking |
|---|---|---|---|---|---|
| VIII | 42.5:42.5:15.0 | 20 | deionized water | 80 | non-lamellar* |

*non-lam. = non-lamellar particles with disordered inner structure consisting of multiply connected bilayers (>90% by weight of amphiphile).

Example 10

Storage Stability

A dispersion consisting of DGMO (2.98 g), GDO (2.0 g), Oleic Acid (OA) (0.13 g) and Pluronic® F127 (0.553 g) in 100.0 g of deionized water was prepared according to the method of Example 2.1. The dispersion was divided into two batches and stored at 25° C. and 4° C. The particle size distribution was measured at regular intervals and found to be consistent with the original size distribution for at least 2 months storage, at 4° C. and 25° C., indicating excellent colloidal and storage stability.

Figure 13:
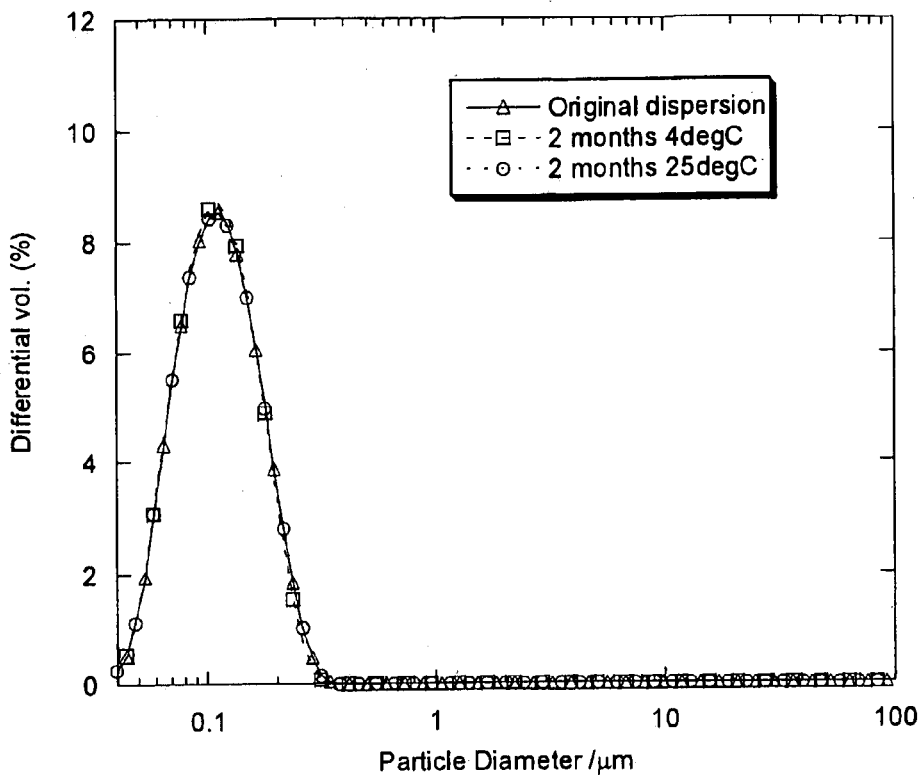
FIG. 13 shows the particle size distributions of a self-dispersed DGMO/GDO/OA/Pluronic® F127 sample after storage for 2 months at 4° C. and 25° C.

No changes of the ratio of non-lamellar to lamellar particles could be observed (by cryo-TEM) during storage. The particle size distributions of the original dispersion and after storage for 2 months at 4° C. and 25° C. are shown in FIG. 13.

Components:

a1 DGMO
a2 OA
b GDO
c Pluronic® F127

| Formulation | a1:a2:b:c | a1a2bc wt % | Medium | aq wt % | Phase after shaking |
|---|---|---|---|---|---|
| IX | 52.6:2.3:35.3:9.8 | 5.4 | deionized water | 94.6 | rev. hex./lam* |

Figure 14:
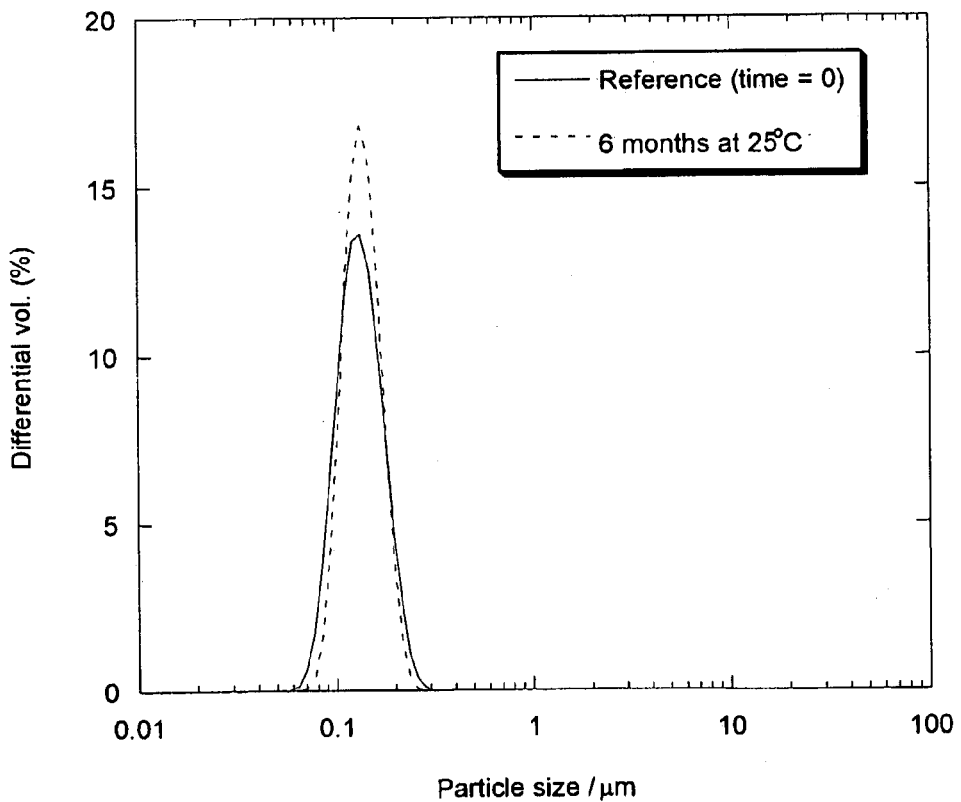
FIG. 14 shows the particle size distributions of a self-dispersed DGMO/GDO/Polysorbate 80 sample after storage for 6 months at 25° C.

*rev. hex./lam = mixed reversed hexagonal (>70% by weight of amphiphile) and lamellar (<30% by weight of amphiphile) particles A dispersion consisting of DGMO (0.934 g), GDO (0.764 g) and P80 (0.302 g) in 38.0 g of deionized water was prepared according to the method of Example 2.1. The particle size distribution was measured at regular intervals and found to be consistent with the original size distribution for at least 6 months storage at 25° C., as shown in FIG. 14.
Components:
a DGMO
b GDO
c Polysorbate 80

| Formulation | a:b:c | abc wt % | Medium | Aq wt % | Phase after shaking |
|---|---|---|---|---|---|
| X | 46.7:38.2:15.1 | 5 | deionized water | 95 | non-lamellar* |

-continued

| Formulation | a:b:c | abc wt % | Medium | Aq wt % | Phase after shaking |
|---|---|---|---|---|---|

*non-lamellar = particles with disordered inner structure consisting of multiply connected bilayers (>90% by weight of amphiphile).

Example 11

Non-lamellar Non-Self-dispersing System (Comparative)

All of the above examples Example 2-10) display non-lamellar reversed phase particles formed by shaking at low speed during 12 h. The resulting dispersions display monomodal, narrow size distributions with the average size being in the submicron range and with a majority of the particles being non-lamellar as evidenced by cryo-TEM. Thus, the dispersions are produced with a minimum of shear/energy input.

To emphasize the difference between the self-dispersing systems in Example 2-10 and conventional dispersions of reversed phase forming lipids, a dispersion of GMO (Rylo™ MG Glycerol Monooleate; DANISCO, Denmark) and Pluronic® F127 (lacking diacyl glycerol component "b") was prepared according to the method of Example 2.1 (12 h shaking at 350 rpm). The ratio of GMO to Pluronic® F127 was 9/1 wt/wt and the total amphiphile concentration was 5 wt %.

Figure 15:
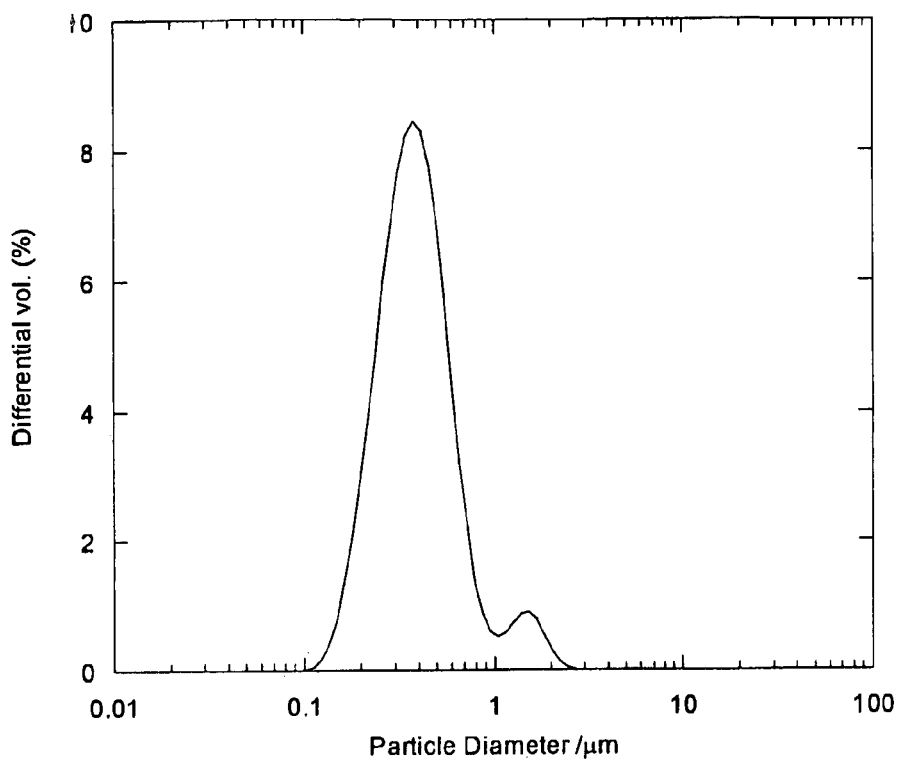
FIG. 15 shows the particle size distribution of a non-self-dispersing GMO/Pluronic® F127 sample.

The resulting coarse dispersion (non-lamellar cubic phase dispersion) was milky white and contained some poorly dispersed material in the form of macroscopic particles. The size distribution of the bulk dispersion is shown in FIG. 15. The size distribution is bimodal with particle sizes in the range from 0.1-2.5 μm. The poorly dispersed material (macroscopic particles >100 μm) is not accounted for in the size distribution shown in FIG. 15.

Example 12

Preparation of Semi-solid Precursor

All components are mixed at 60-70° C. or higher until dissolved (clear homogeneous solution). The solution is cooled to room temperature or to a lower temperature to allow the matrix to solidify. Gelatine capsules filled with the semi-solid precursors fully disintegrate (according to USP method) in water or in any simulated gastrointestinal fluid within 20-30 minutes.

| Composition examples (in % w/w): | | | | | | | |
|---|---|---|---|---|---|---|---|
| Formulation | DGMO | GDO | P80 | PEG 4000 | progesterone | cyclosporin | fenofibrate | ketoconazole |
| 1 | 20 | 20 | 10 | 50 | | | | |
| 2 | 18 | 18 | 9 | 45 | 10 | | | |
| 3 | 18 | 18 | 9 | 45 | | 10 | | |
| 4 | 18 | 18 | 9 | 45 | | | 10 | |
| 5 | 18 | 18 | 9 | 45 | | | | 10 |

Example 13

Surface Functionalization

The particle surface was functionalized by preparing a composition by the method of Example 2.1 comprising DGMO (1.77 g), GDO (1.17 g) and DOPG (0.077 g). The components were molecularly mixed by heating for 5 min at 70° C. and vortexing. The homogenous lipid melt (2.5 g) was added drop wise to 22.5 g of deionized water containing Pluronic® F127 (0.277 g). The resulting coarse dispersion was put on a shaking table and shaken for 12 hours to give a white homogenous dispersion. The particles were functionalized with Chitosan (Pronova Biopolymer, Norway) by adding 0.52 g of a 4 wt % Chitosan solution (Chitosan dissolved in 0.5 wt % acetic acid) to the lipid dispersion and equilibrating the solution for 1 h.

The above non-lamellar Chitosan-functionalized dispersion was further treated to provide a dried powder precursor using a Spray-Drier (BÜCHI Mini Spray Dryer B-290). The dispersion was spray-dried in the presence of trehalose (Sigma-Aldrich, Sweden) to give a fine white powder.

Example 14

Preparation of a Gel Containing Non-lamellar Particles

A gel containing self-dispersed non-lamellar particles was prepared by adding 5 mg Sodium hyaluronate (Sigma-Aldrich, Sweden) to 1 g of a 20 wt % dispersion of non-lamellar particles prepared by the method of Example 2.1 with the following composition: DGMO (42.5 wt %), GDO (42.5 wt %) and P80 (15 wt %). The resulting mixture was stirred at low speed for 24 h forming a turbid and viscous gel.

Example 15

Active Agent Loading

A composition comprising DGMO (54% by weight), GDO (36% by weight) and Pluronic® F127 (10% by weight) was dispersed in 99 times its weight in water by the method of Example 2.1.

The dispersion was divided into samples and loaded with each of the active agents shown below by each of two techniques:
i) A saturated solution of active was equilibrated with the particles in dispersion at 37° C. for three days by gentle stirring on a rotating table.
ii) The samples were dispersed in a solution of excess active agent and heat treated by autoclavation at 125° C. for 20 minutes and were allowed to temperature equilibrate at 37° C. for at least one hour.

The following loadings were achieved, expressed as percentage active agent incorporated relative to the mass of total amphiphile.

| Active Agent | % loading by equilibration | % loading by heat treatment |
|---|---|---|
| Progesterone | 2.99 | 12.65 |
| Fenofibrate | 3.3 | 7.12 |
| Fulvestrant | 0.6 | 3.76 |
| Ketoconazole | 3.49 | 19.25 |

Example 16

Further Active Agent Loading

Figure 16:
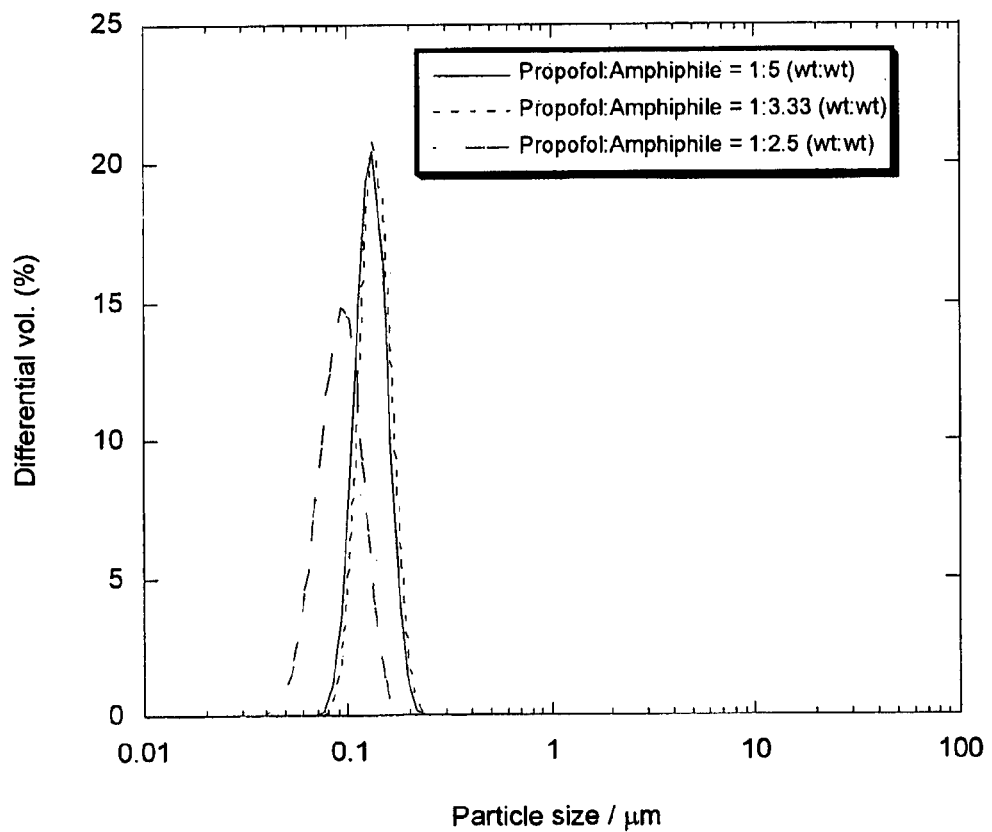
FIG. 16 shows the particle size distributions of self-dispersed DGMO/GDO/Polysorbate 80 samples with varying Propofol loading.
Figure 17:
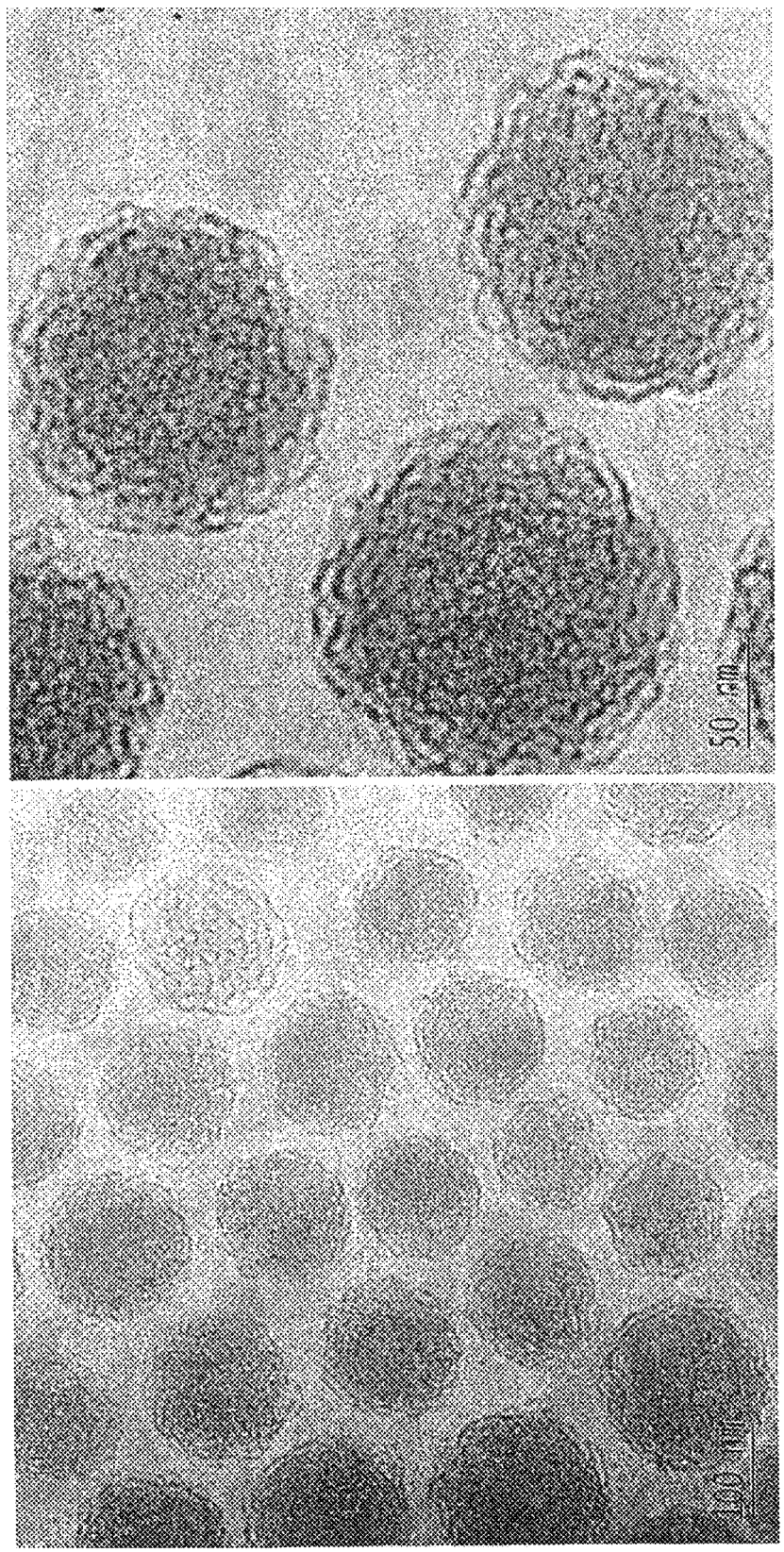
FIG. 17 shows cryo-transmission electron micrographs of a self-dispersed DGMO/GDO/Polysorbate 80 sample (100 mg amphiphile/mL) containing 20 mg Propofol/mL.

Non-lamellar particle dispersions containing the anaesthetic active agent Propofol (Sigma-Aldrich, Sweden) were formed by mixing a composition comprising DGMO (42.5% by weight of amphiphile), GDO (42.5% by weight of amphiphile) and P80 (15% by weight of amphiphile) with Propofol at the proportions indicated in the table below. The components were molecularly mixed by heating for 5 min at 70° C. and vortexing. The homogenous lipid/Propofol melt was added drop wise to an aqueous solution containing 2.5% (by weight of total formulation) of Glycerol (Apoteket, Sweden). The resulting coarse dispersions were put on a shaking table (350 rpm) and shaken for 12 hours to give homogenous dispersions. The dispersions were filtered through a 0.2 μm filter and heat-treated by the method of Example 2.2. The particle size distributions of the resulting dispersions were narrow and monomodal with mean particle sizes in the range of 100-150 nm as shown in FIG. 16. The morphology of the Propofol loaded particles was investigated using cryo-TEM. As shown in FIG. 17, the cryo-TEM images reveal that the non-lamellar inner particle structure of multiply connected bilayers is retained after Propofol loading (compare with FIG. 6). The Propofol loaded dispersions were found to be stable to storage at room temperature for at least 1 month.

Table with compositions of the final non-lamellar particle/ Propofol dispersions:

| Amphiphile conc. (mg/mL) | Propofol conc. (mg/mL) | Propofol:Amphiphile (wt:wt) |
|---|---|---|
| 100 | 20 | 1:5 |
| 100 | 30 | 1:3.33 |
| 50 | 20 | 1:2.5 |

Example 17

Pharmacodynamics and Pharmacokinetics of Propofol Loaded into Non-lamellar Particles A dispersion of non-lamellar particles containing Propofol was prepared with the same composition and by the same method as in Example 16 except that the Propofol concentration in this case was 10 mg/mL and the amphiphile concentration was 100 mg/mL. The non-lamellar particle Propofol dispersion was compared for duration of anaesthesia and pharmacokinetics in rats (male SPF Sprague-Dawley rats (Mol: SPRD HAN, M&B Taconic, Lille Skensved, Denmark)) with the reference commercial Propofol Fresenius Kabi emulsion formulation (10 mg Propofol/mL). The animals were given a single bolus intravenous injection of 10 mg Propofol per kg body weight (induction of anaesthesia occurred directly after injection in both cases). For pharmacodynamic parameters, the time to recover (righting response time indicated by attempts to stand up) was recorded. The results are summarized in the table below indicating the high efficiency of the non-lamellar particle Propofol dispersion to maintain the required anaesthetic effect.

Table with pharmacodynamic parameters:

| Formulation | Number of rats | Average Recovering Time (sec) (Std. Dev.) |
|---|---|---|
| Propofol Fresenius Kabi | 5 | 531 (53) |
| Non-lamellar Particle Propofol Dispersion | 5 | 706 (111) |

Figure 18:
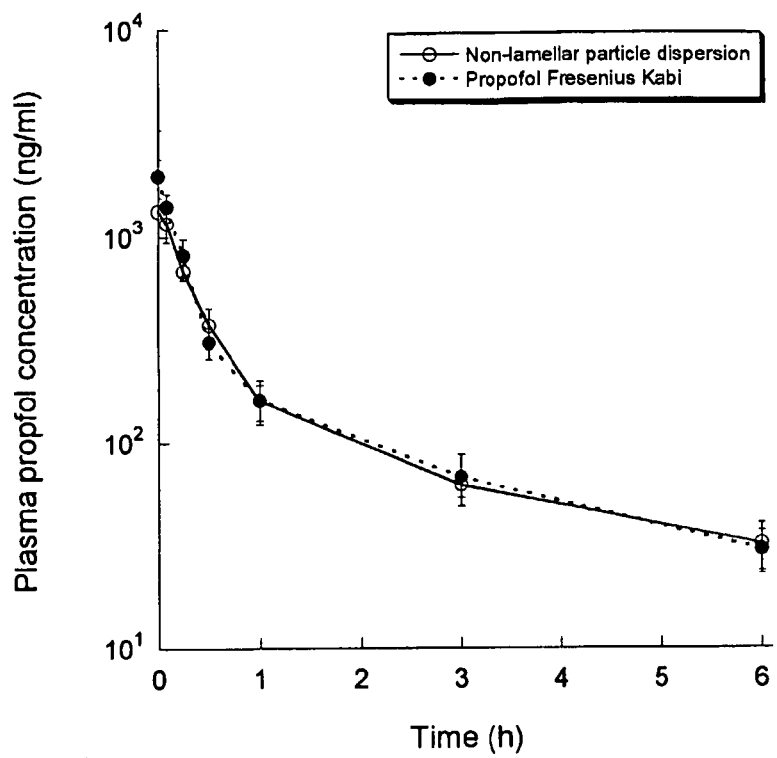
FIG. 18 shows plasma concentration over time for Propofol administered in a non-lamellar nanoparticle dispersion or as the commercially available Propofol Fresenius Kabi product.

Blood samples (0.3 mL) were collected pre-dose (one day before dosing), 5 minutes, 15 minutes, 30 minutes, 1 hr, 3 hrs, 6 hrs and 24 hrs after dosing. The Propofol concentration in rat plasma was determined by a high pressure liquid chromatography (HPLC) method known to scientists skilled in the art. Plasma concentration over time of propofol was similar for the reference formulation and the non-lamellar particle propofol formulation, respectively (FIG. 18). Also, exposure to the drug after bolus i.v. injection assessed as area-under-the-curves from 0 to eternity ($AUC_\infty$) when data was fitted to a 1-compartment pharmacokinetic model (Model FitMacoIVBolus; Kinetica 4.3, InnaPhase Corp., Philadelphia, Pa., USA) was similar; the non-lamellar particle propofol $AUC_\infty$ was 96% of the reference formulation (P=0.670; t-test). The terminal elimination half-life was also similar between treatments ($t_{1/2\beta}$=3.1±0.78 hrs (SD) and 2.5±0.77 hrs, for the non-lamellar particle and reference formulation, respectively). However, the initial half-life of the curve (distribution phase) was slightly but significantly (P=0.028; t-test) greater for the non-lamellar formulation (($t_{1/2\alpha}$=0.22±0.05 hrs and 0.15±0.02 hrs, for the non-lamellar particle and reference formulation, respectively). The increased initial half-life may suggest an increased circulation time of the drug carrier and/or a decreased release rate for the drug. This may also explain the prolonged average recovering time after induction of anaesthesia (see table above). An alternative explanation is a more effective absorption of Propofol across the blood-brain barrier facilitated by the non-lamellar particles.

Example 18

Further Active Agent Loading

A homogenous liquid solution containing the anti-inflammatory local anaesthetic agent Benzydamine hydrochloride (Sigma-Aldrich, Sweden) was prepared by molecularly mixing 6.8 mg of Benzydamine hydrochloride with 1.0 g of a mixture of DGMO/GDO/Polysorbat 80 (42.5/42.5/15 wt %) employing gentle stirring over night at room temperature. A 30 wt % lipid dispersion of non-lamellar particles was formed by vortexing this solution together with 2.3 g of deionized water.

Example 19

Figure 19:
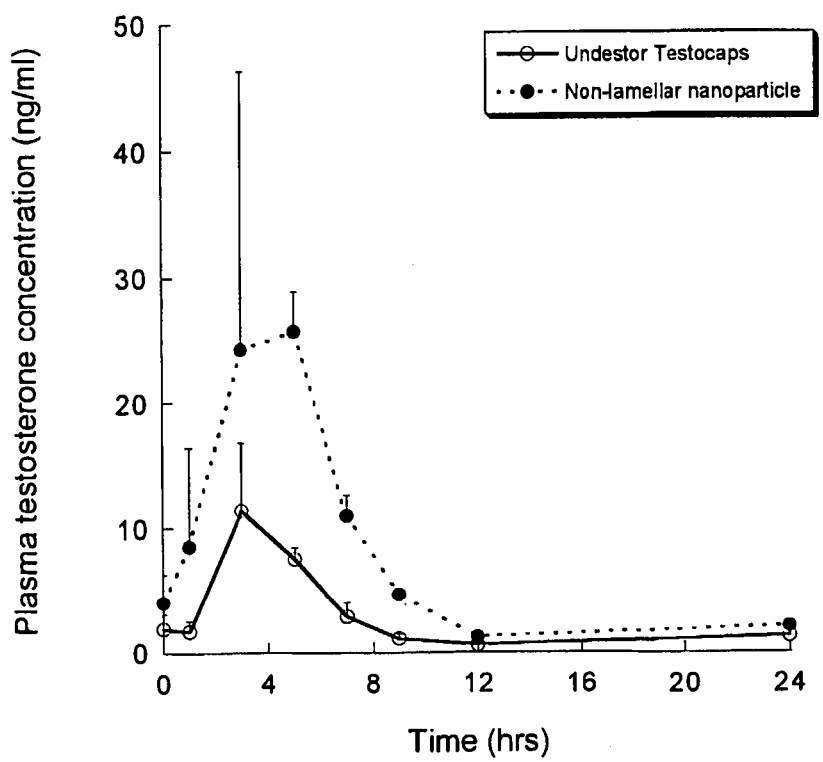
FIG. 19 shows the plasma testosterone concentration over time for the reference Undestor Testocaps and the non-lamellar nanoparticle testosterone undecanoate, respectively.

Loading of Testosterone Undecanoate (TEU) and Oral Bioavailability of TEU Formulated in Liquid Non-lamellar Phase Precursor A homogenous liquid formulation of the hormone testosterone undecanoate (TEU) was prepared by dissolving 0.24 g TEU in a liquid non-lamellar phase precursor mixture comprising DGMO (0.75 g), GDO (0.75 g) and P80 (0.26 g). The sample was allowed to mix with gentle stirring for 3 h. The liquid non-lamellar particle precursor containing TEU was compared for bioavailability of TEU in rats with the reference commercial Undestor Testocaps (Apoteket, Sweden). The animals were given the liquid formulations with the TEU at a dose of 100 mg TEU per kg bodyweight. Blood samples (0.3 mL) were collected pre-dose, 1 hr, 3 hrs, 5 hrs, 7 hrs, 9 hrs, 12 hrs and 24 hrs. Concentration of testosterone (TES) in plasma was quantified using a commercial assay. Briefly, the principle of the assay is a competitive ELISA where an unknown amount of antigen (TES) in a sample competes for the binding sites of antibodies coated onto the microtiter wells with a fixed amount of added enzyme-labelled antigen. The assay showed no cross-reactivity with TEU. Plasma concentration of TES after administration of TEU in the non-lamellar nanoparticle formulation was significantly greater than for the commercial reference formulation (FIG. 19). Bioavailability for the non-lamellar testosterone undecanoate assessed as the ratio between the area-under-the-concentration vs. time curves from 0 to 24 hrs ($AUC_{0-24h}$), using the trapezoidal method, was significantly (P<0.05; t-test) increased by a factor 2.7 compared to the reference. Similarly, $C_{max}$ was increased 2.4 times (P<0.05; t-test).

Example 20

Loading of the Peptide Octreotide (OCT) and Oral Bioavailability of OCT Formulated in the Non-lamellar Phase Dispersion 20.1—Loading of Octreotide in Non-lamellar Nanoparticles A dispersion of non-lamellar particles containing the peptide active Octreotide (OCT) (PolyPeptides, Sweden) was formed by mixing 1.767 g of DGMO, 1.168 g of GDO, 0.077 g of DOPG and 0.00657 g of OCT. The components were molecularly mixed by heating for 5 min at 70° C. and vortexing. The homogenous lipid/OCT melt (2.505 g) was added drop wise to a solution containing 0.2771 g of Pluronic® F127 and 22.5282 g of deionized water. The resulting coarse dispersion was put on a shaking table (350 rpm) and shaken for 12 hours to give a white homogenous dispersion. The dispersion was thereafter heat-treated by the method of Example 2.2. To the heat-treated dispersion was added 0.52 g of a 4 wt % solution of Chitosan (Chitosan dissolved in 0.5% acetic acid) and the dispersion was allowed to equilibrate for 12 h before oral administration to the animals.

20.2—Animal Studies—General Procedure

On the first day of the experiment, the rats were prepared by inserting a silicon catheter (OD approx. 1 mm) in the jugular vein under isoflurane anaesthesia. The catheter was tunnelled under the skin and exteriorised between the scapulae. After surgery the rats were allowed 48 hours of recovery before dosing. The catheter was rinsed with 0.9% NaCl containing 1 mM EDTA, every morning during the recovery period.

In the morning, after approximately 16 hours of fasting (water was accessible), the animals were dosed and blood collected. The animals were allowed free access to water after dosing, but had no access to food. After the last sampling, all animals were sacrificed.

20.3—Dosing

The rats were dosed intravenously through the venous catheter or by gavage by a plastic ball-tipped gavage tube. Intravenously dosed rats were given 0.2 mg OCT per kg bwt in 1.0 mL/kg of sterile saline and gavaged rats were given the dispersion in water of OCT-containing non-lamellar particles or a saline solution of OCT to a dose of 3 mg OCT per kg bwt (dose volume equal to 10 mL per kg bwt). Oral dosing was performed under light isoflurane anaesthesia.

20.4—Sampling

Blood samples (0.5 mL) were collected pre-dose (one day before dosing), 10 minutes, 30 minutes, 1 hr, 3 hrs, 6 hrs and 24 hrs after dosing in EDTA-treated test tubes also containing 500 KIE aprotinin (Trasylol®) per mL sample. All blood samples were gently mixed and held on ice (maximally 10 minutes) before they were centrifuged at 2,000 g for 10 minutes at +4° C. Plasma were then immediately transferred to new test tubes and put on dry ice. Samples were stored at −80° C. until analysis.

20.5—Analysis

The content of OCT in all plasma samples was measured by a competitive immunoassay. Briefly, the OCT peptide coated on a microplate competes for the antibody in solution with the OCT present in the plasma sample. The fraction of antibody remaining in solution is removed, and the fraction bound to the immobilized peptide is quantified, the signal obtained being inversely proportional to the concentration of OCT in the sample.

Plasma OCT concentration data were utilized to calculate area-under-the-curve from 0 to 6 hours (AUC) by the trapezoidal method.

Dose-corrected absolute bioavailability of OCT in the oral non-lamellar formulation was calculated as:

$$\text{Availability } (F) = (AUC_{oral} \times \text{Dose}_{IV}) / (AUC_{IV} \times \text{Dose}_{oral}) \times 100$$

20.6—Results

Rats were dosed with an intravenous OCT solution, and orally with the dispersion of OCT-containing non-lamellar particles and OCT in a saline solution, according to the above described method. Plasma OCT contents were analysed and OCT plasma concentrations were plotted over time. Absolute bioavailability (F) of OCT administered orally in the non-lamellar nanoparticles was around 0.4%, while OCT delivered in the pure saline solution resulted in bioavailability of approx. 0.04%. Hence, the non-lamellar dispersion has an enhancing effect of around a factor 10 for the oral bioavailability of OCT compared to the pure saline solution.

The invention claimed is:

1. A composition which self-disperses upon contact with an aqueous fluid to provide colloidal non-lameller particles having at least an internal region adopting a non-lamellar phase structure and having a monomodal size distribution with an average particle size of no more than 5 µm, said composition comprising
    a) at least one monoacyl lipid, wherein said component a) consists of a monoacyl lipid or mixture of monoacyl lipids which forms a micellar or lamellar phase upon contact with water;
    b) at least one diacyl glycerol, at least one tocopherol, or mixtures thereof, wherein said component b) comprises at least one diacyl glycerol with acyl groups each having 12 to 22 carbon atoms and between 0 and 3 unsaturations, or at least one tocopherol, or mixtures thereof and
    c) at least one fragmentation agent, wherein said component c) is selected from polymeric fragmentation agents, polyol surfactants, proteins, anionic surfactants, cationic surfactants, monoacyl lipids and mixtures thereof; and optionally an active agent;
    wherein a/(a+b), being the ratio by weight of component a) to the sum of components a) and b) is between 0.2 and 0.9;
    c/(a+b+c), being the ratio by weight of component c) to the sum of components a), b) and c), is between 0.01 and 0.3.

2. A composition as claimed in claim 1 wherein said non-lamellar particles are reversed hexagonal liquid crystalline particles.

3. A composition as claimed in claim 1 wherein, upon self dispersion, at least 50% by weight of components a), b) & c) are present as non-lamellar particles.

4. A composition as claimed in claim 1 wherein said colloidal particles have a monomodal size distribution with an average particle size of no more than 5 µm.

5. A composition as claimed in claim 1 wherein said component a) comprises at least one monoacyl oligoglycerol.

6. A composition as claimed in claim 1 wherein said component b) forms an oil or L2 phase upon contact with water and consists of at least one component selected from diacyl glycerols, mixtures of diacyl glycerols, tocopherols and mixtures of tocopherols.

7. A composition as claimed in claim 1 wherein component a) comprises diglycerolmonooleate and component b) comprises glyceroldioleate.

8. A composition as claimed in claim 1 additionally comprising at least one component selected from charged lipids, surfactants, polymeric solidifying agents and polymeric surface modifiers.

9. A composition as claimed in claim 1 containing no organic solvent or hydrotrope.

10. A composition as claimed in claim 1 containing up to 15% by weight of an organic solvent.

11. A composition as claimed in claim 1 comprising a shear-sensitive and/or heat-sensitive active agent.

12. A composition as claimed in claim 1 comprising at least one active agent selected from progesterone, fenofibrate, fulvestrant, ketoconazole benzydamine, propofol, octreotide, and testosterone undecanoate.

13. A composition as claimed in claim 1 wherein component b) consists of a diacyl glycerol or mixtures thereof.

14. A pharmaceutical formulation comprising a composition as claimed in claim 1 and at least one pharmaceutically acceptable carrier or excipient.

15. A pharmaceutical formulation as claimed in claim 14 wherein said formulation consists of at least 50% by weight of the composition, no more than 10% by weight total organic solvent, including any solvent present in said composition, and the remainder aqueous solvents and/or pharmaceutically acceptable formulating agents.

16. A pharmaceutical formulation as claimed in claim 14 wherein said formulation is suitable for oral administration.

17. Colloidal non-lamellar particles comprising
    a) at least one monoacyl lipid, wherein said component a) consists of a monoacyl lipid or mixture of monoacyl lipids which forms a micellar or lamellar phase upon contact with water;
    b) at least one diacyl glycerol, at least one tocopherol, or mixtures thereof, wherein said component b) comprises at least one diacyl glycerol with acyl groups each having 12 to 22 carbon atoms and between 0 and 3 unsaturations, or at least one tocopherol, or mixtures thereof and
    c) at least one fragmentation agent, wherein said component c) is selected from polymeric fragmentation agents, polyol surfactants, proteins, anionic surfactants, cationic surfactants, monoacyl lipids and mixtures thereof; optionally an active agent and optionally an aqueous fluid;
    wherein said colloidal particles have at least an internal region adopting said non-lamellar phase structure and have a monomodal size distribution with an average particle size of no more than 5 µm;
    wherein a/(a+b), being the ratio by weight of component a) to the sum of components a) and b) is between 0.2 and 0.9;
    c/(a+b+c), being the ratio by weight of component c) to the sum of components a), b) and c), is between 0.01 and 0.3.

18. Colloidal non-lamellar particles as claimed in claim 17 formed or formable from a composition.

19. Colloidal non-lamellar particles as claimed in claim 17 wherein said particles are stable to storage in dispersion in an aqueous solvent for at least 10 days.

20. Colloidal non-lamellar particles as claimed in claim 17 wherein fragmentation agent c) comprises at least one monoacyl lipid.

21. A kit for the preparation of a dispersion of non-lamellar particles, said kit comprising a composition comprising;
    a) at least one monoacyl lipid, wherein said component a) consists of a monoacyl lipid or mixture of monoacyl lipids which forms a micellar or lamellar phase upon contact with water;
    b) at least one diacyl glycerol, at least one tocopherol, or mixtures thereof, wherein said component b) comprises at least one diacyl glycerol with acyl groups each having 12 to 22 carbon atoms and between 0 and 3 unsaturations, or at least one tocopherol, or mixtures thereof and
    c) at least one fragmentation agent, wherein said component c) is selected from polymeric fragmentation agents, polyol surfactants, proteins, anionic surfactants, cationic surfactants, monoacyl lipids and mixtures thereof; and optionally an active agent;

wherein said colloidal particles have at least an internal region adopting said non-lamellar phase structure and have a monomodal size distribution with an average particle size of no more than 5 μm;

wherein a/(a+b), being the ratio by weight of component a) to the sum of components a) and b) is between 0.2 and 0.9;

c/(a+b+c), being the ratio by weight of component c) to the sum of components a), b) and c), is between 0.01 and 0.3.

22. A method for the formation of a dispersion of non-lamellar particles, said method comprising contacting a composition comprising
   a) at least one monoacyl lipid, wherein said component a) consists of a monoacyl lipid or mixture of monoacyl lipids which forms a micellar or lamellar phase upon contact with water;
   b) at least one diacyl glycerol, at least one tocopherol, or mixtures thereof, wherein said component b) comprises at least one diacyl glycerol with acyl groups each having 12 to 22 carbon atoms and between 0 and 3 unsaturations, or at least one tocopherol, or mixtures thereof and
   c) at least one fragmentation agent, wherein said component c) is selected from polymeric fragmentation agents, polyol surfactants, proteins, anionic surfactants, cationic surfactants, monoacyl lipids and mixtures thereof;

wherein said colloidal particles have at least an internal region adopting said non-lamellar phase structure and have a monomodal size distribution with an average particle size of no more than 5 μm;

wherein a/(a+b), being the ratio by weight of component a) to the sum of components a) and b) is between 0.2 and 0.9;

c/(a+b+c), being the ratio by weight of component c) to the sum of components a), b) and c), is between 0.01 and 0.3; and with an aqueous fluid and optionally subjecting the thus-formed mixture to a low energy agitation method.

* * * * *